(12) United States Patent
Horne et al.

(10) Patent No.: US 9,828,342 B2
(45) Date of Patent: Nov. 28, 2017

(54) ISATIN DERIVATIVES, PHARMACEUTICAL COMPOSITIONS THEREOF, AND METHODS OF USE THEREOF

(71) Applicants: CITY OF HOPE, Duarte, CA (US); THE REGENTS OF THE UNIVERSITY OF CALIFORNIA, Oakland, CA (US)

(72) Inventors: David A. Horne, Altadena, CA (US); Richard Jove, Glendora, CA (US); Christopher Lincoln, La Canada, CA (US); Sangkil Nam, Monrovia, CA (US); Larry Overman, Irvine, CA (US); Jun Xie, Duarte, CA (US)

(73) Assignees: CITY OF HOPE, Duarte, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 312 days.

(21) Appl. No.: 13/776,374

(22) Filed: Feb. 25, 2013

(65) Prior Publication Data
US 2013/0225637 A1 Aug. 29, 2013

Related U.S. Application Data

(60) Provisional application No. 61/602,874, filed on Feb. 24, 2012.

(51) Int. Cl.
C07D 209/38 (2006.01)
C07D 401/10 (2006.01)
C07D 401/04 (2006.01)

(52) U.S. Cl.
CPC ......... C07D 209/38 (2013.01); C07D 401/04 (2013.01); C07D 401/10 (2013.01)

(58) Field of Classification Search
CPC .......................... C07D 209/38; C07D 401/10
See application file for complete search history.

(56) References Cited

U.S. PATENT DOCUMENTS 4,322,533 A * 3/1982 Lesher et al. ............. 546/277.7

OTHER PUBLICATIONS

Ellis et al., Journal of Organic Chemistry, 2008;73:9151-9154.*

(Continued)

*Primary Examiner* — San-Ming Hui
(74) *Attorney, Agent, or Firm* — Perkins Coie LLP; Yingli Wang

(57) ABSTRACT

One aspect of the invention relates to novel isatin derivative compounds and the pharmaceutical composition thereof. Another aspect of the invention relates to methods of using the isatin derivative compounds disclosed herein and the pharmaceutical compositions thereof. In certain embodiments, the method is used to treat a cancer or a tumor in a subject including, without limitation, prostate cancer, melanoma, pancreatic cancer, ovarian cancer, and lymphoma. In certain embodiment, the method is used to treat a condition in a subject that can be regulated by the activation of one or more proteins such as EGFR, Erk1/2, Her2/Neu, Jak2, Src, Stat3, Akt, Cyclin B1, and Cdc25C. In certain embodiment, the method is used to treat a condition in a subject that can be regulated by the disruption of microtubule formations.

8 Claims, 17 Drawing Sheets

(56) References Cited

OTHER PUBLICATIONS

Figure 1:
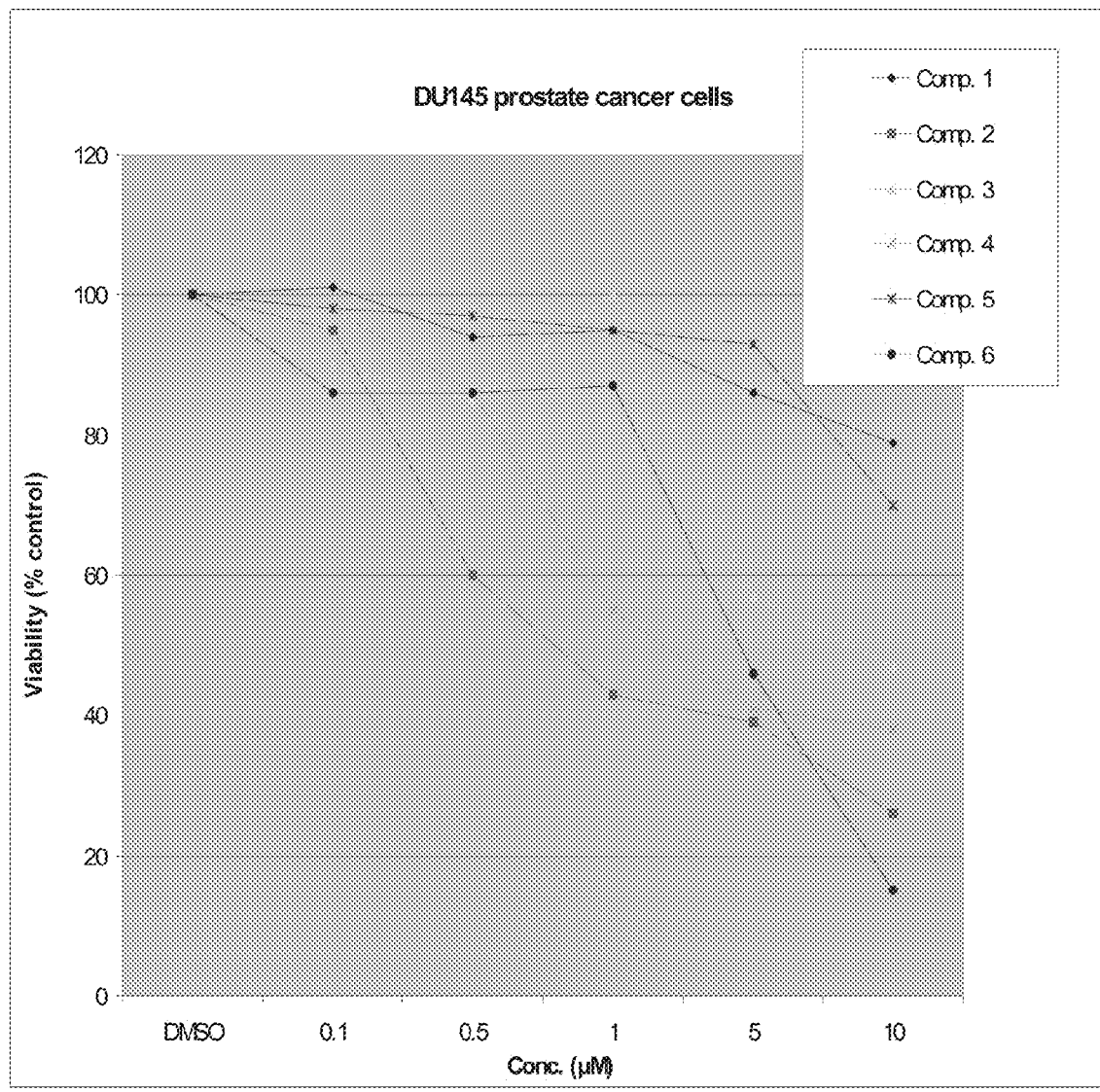

Aboul-Fadl, T., Mohammed FA, Hassan EA., Synthesis, Antitubercular Activity and Pharmacokinetic Studies of Some Schiff Bases Derived from 1-Alkylisatin and Isonicotinic Acid Hydrazide (INH), Arch. Pharm. Res., 26:778-784 (2003).

Beraldo, H., et al., "The Wide Pharmacological Versatility of Semicarbazones, Thiosemicarbazones and Their Metal Complexes," Mini-Rev. Med. Chem. 4:31-39 (2004).

Chiyanzu, I., Clarkson C, Smith PJ, Lehman J, Gut J, Rosenthalc PJ, Chibalea K., Design, synthesis and antiplasmodial evaluation in vitro of new 4-aminoquinoline isatin derivatives, Bioorg. Med. Chem. 13:3249-3261 (2005).

Cocco, M.T., Congiu C, Onnis V, Pusceddu MC, Schivo ML, Logu A., Synthesis and antimycobacterial activity of some isonicotinoylhydrazones. Eur. J. Med. Chem., 34:1071-1076 (1999).

El-Sawi, E.A., Mostaza TB, Mostaza BB, Studies on the molluscicidal action of some isatin derivatives against Biomphalaria alexandrina in Egypt. J. Egypt. Soc. Parasitol., 28:481-486 (1998).

Epstein, D.A., Marsh YV, Van der Pas M, Feigner PL, and Schreiber AB., Biological activity of liposome-encapsulated murine interferon gamma is mediated by a cell membrane receptor. Proc. Natl. Acad. Sci. (USA), 82:3688-3692 (1985).

Fedchenko, V., Globa A, Kaloshin A, Kapitsa I, Nerobkova L, Val'dman E, Buneeva O, Glover V, Medvedev A., The effect of short-term administration of (−)-deprenyl and isatin on the expressions of some genes in the mouse brain cortex, Med. Sci. Monit. 14:69-73 (2008).

Gaston, M.A., Dias LRS, Freitas ACC, Miranda ALP, Barreiro EJ., Synthesis and analgesic properties of new 4-arylhydrazone 1-H pyrazole [3,4-b] pyridine derivatives, Pharmac. Acta Helvet., 71:213-219 (1996).

Hamada, T., Okuno Y, Ohmori M, Nishi T, and Yonemitsu O., Photochemical Synthesis of 1, 2, 3, 4-Tetrahydroisoquinolin-3-ones and Oxindoles from N-Chloroacetyl Derivatives of Benzylamines and Anilines. Role of Intramolecular Exciplex Formation and cis Conformation of Amide Bonds, Chem. Pharm. Bull., 29:128-136 (1981).

Holla, B.S., Rao BS, Shridhara K, Akberali PM., Studies on arylfuran derivatives. Part XI. Synthesis, characterization and biological studies on some Mannich base carrying 2, 4-dichlorophenylfurfural moiety, II Farmaco, 55:338-344 (2000).

Imam, S.A., Varma RS., Isatin-3-anils as excystment and cysticidal agents against Schizopyrenus russelli, Experientia, 31:287-1288 (1975).

Karah, N., Terzioglu N, Gursoy A., Synthesis and structure-activity relationships of 3-hydrazono-1H-2-indolinones with antituberculosis activity, Arzneim-Forsch/Drug. Res., 48:758-763 (1998).

Karali, N., Kocabalkanli A, Gürsoy A, Ateş Ö., Synthesis and antitubercular activity of 4-(3-coumarinyl)-3-cyclohexyl-4-thiazolin-2-one benzylidenehydrazones, II Farmaco, 57:589-593 (2002).

Koçyigit, K., Kaymakçioǧlu BK, Rollas S., Synthesis, characterization and evaluation of antituberculosis activity of some hydrazones, II Farmaco, 57:595-599 (2002).

Küçükgüzel, S.G., Rollas S, Küçükgüzel I, Kiraz M., Synthesis and antimycobacterial activity of some coupling products from 4-aminobenzoic acid hydrazones, Eur. J. Med. Chem., 34:1093-1100 (1999).

Langer, R., Brem H, and Tapper D., Biocompatibility of polymeric delivery systems for macromolecules, J. Biomed. Mater. Res., 15:267-277 (1981).

Logan, J.C., Fox MP, Morgan JH, Makohon AM, Pfau CJ., Arenavirus inactivation on contact with N-substituted isatin β-thiosemicarbazones and certain cations, J. Gen. Virol., 28:271-283 (1975).

Loncle, C., Brunel JM, Vidal N, Dherbomez M, Letourneux Y., Synthesis and antifungal activity of cholesterol-hydrazone derivatives, Eur. J. Med. Chem., 39:1067-1071 (2004).

Maccari, R., Ottaná R, Vigorita MG, In vitro advanced antimycobacterial screening of isoniazid-related hydrazones, hydrazides and cyanoboranes: Part 14, Bioorg. Med. Chem. Lett., 15:2509-2513 (2005).

Marti, C. and Carreira EM. Carreira, E. M., Total Synthesis of (−)-Spirotryprostatin B: Synthesis and Related Studies, J. Am. Chem. Soc. 2005, 127, 11505-11515.

Melnyk, P., Leroux V, Sergheraert C, Grellier P., Design, synthesis and in vitro antimalarial activity of an acylhydrazone library. Bioorg. Med. Chem. Lett., 16:31-35 (2006).

Molander, G.A., and Ellis N., Acc. Organotrifluoroborates: Protected Boronic Acids That Expand the Versatility of the Suzuki Coupling Reaction, Chem. Res., 40:275-286 (2007).

Overman, L.E., and Peterson EA., Enantioselective synthesis of (−)-idiospermuline, Tetrahedron, 59:6905-6919 (2003).

Pal, R., Jain K, Gupta GD, Handa RN, Puzari HK., Synthetic methods using isatin and derivatives, Indian J Chem. 19991, 30B:1098.

Pandeya, S.N., Smitha S, Jyoti M, Sridhar SK., Biological activities of isatin and its derivatives. Acta Pharm., 55:27-46 (2005).

Pandeya, S.N., Sriram D, Nath G, De Clercq E., Synthesis, antibacterial, antifungal and anti-HIV activities of Schiff and Mannich bases derived from isatin derivatives and N-[4-(4'-chlorophenyl)thiazol-2-yl] thiosemicarbazide, Eur. J. Pharm. Sci., 9:25-31 (1999).

Pandeya, S.N., Sriram D, Nath G, De Clercq E., Synthesis, antibacterial, antifungal and anti-HIV activity of Schiff and Mannich bases of isatin with N-[6-chlorobenzthiazole-2-yl] thiosemicarbazide, Indian J. Pharm. Sci., 61:358-361 (1999).

Pandeya, S.N., Sriram D, Nath G, De Clercq E., Synthesis, antibacterial, antifungal and anti-HIV evaluation of Schiff and Mannich bases of isatin derivatives with 3-amino-2-methylmercapto quinazolin-4(3H)-one, Pharm. Acta Helv., 74:11-17 (1999).

Pandeya, S.N., Sriram D, Nath G, De Clercq E., Synthesis, antibacterial, antifungal and anti-HIV activities of Norfloxacin Mannich bases, Eur. J. Med. Chem., 35:249-255 (2000).

Pandeya, S.N., Sriram D, Nath G, De Clercq E., Synthesis, antibacterial, antifungal and anti-HIV evaluation of Schiff and Mannich bases of isatin and its derivatives with triazole. Arzneim. Forsch. /Drug Res., 50:55-59 (2000).

Pandeya, S.N., Sriram D., Synthesis and screening for antibacterial activity of Schiff's and Mannich bases of Isatin and its derivatives, Acta. Pharm. Turc., 40:33-38 (1998).

Papakonstantinou-Garoufalias, S., Pouli N, Marakos P, Chytyroglou-Ladas A., Synthesis antimicrobial and antifungal activity of some new 3-substituted derivatives of 4-(2,4-dichlorophenyl)-5-adamantyl-1H-1,2,4-triazole, II Farmaco, 57:973-977 (2002).

Patole, J., Sandbhor U, Padhye S, Deobagkar DN, Anson CE, Powell A., Structural chemistry and In Vitro Antitubercular Activity of Acetylpyridine Benzoyl Hydrazone and Its Copper Complex against *Mycobacterium smegmatis*, Bioorg. Med. Chem. Lett., 13:51-55 (2003).

Popp, F.D., Potential anticonvulsant. XII. Anticonvulsant activity of some aldehyde derivatives, Eur. J. Med. Chem., 24:313-315 (1989).

Rando, D.G., Sato DN, Siqueira L, Malvezzi A, Leite CQF, Amaral AT, Ferreira EI, Tavares LC, Potential Tuberculostatic Agents. Topliss Application on Benzoic Acid [(5-Nitro-thiophen-2-yl)-methylene]-hydrazide Series, Bioorg. Med. Chem., 10:557-560 (2002).

Sarangapani, M., Reddy VM., Synthesis and antimicrobial activity of 1-[(N, N-disubstituted amino) methyl]-3-[(2-phenyl-3, 4-dihydro-4-oxoquinazoline-3-yl] in-dole-2-one, Indian J. Heterocycl. Chem., 3:257-260 (1994).

Sarciron, M.E., Audin P, Delebre I, Gabrion C, Petavy AF, Paris J., Synthesis of propargylic alcohols and biological effects on Echinococcus multilocularis metacestodes, J. Pharm. Sci., 82:605-609 (1993).

Sidman, K.R., Steber WD, Schwope AD and Schnaper GR., Controlled Release of Macromolecules and Pharmaceuticals from Synthetic Polypeptides Based on Glutamic Acid, Biopolymers, 22:547-556 (1983).

(56) References Cited

OTHER PUBLICATIONS

Singh, S.P., Shukla SK, Awasthi LP., Synthesis of some 3-(4'-nitrobenzoylhydrazono)-2-indolinones as a potential antiviral agents. Curr. Sci., 52:766-769 (1983).

Sriram, D., Yogeeswari P, Gopal G., Synthesis, anti-HIV and antitubercular activities of lamivudine prodrugs, Eur. J. Med. Chem., 40:1373-1376 (2005).

Todeschini, A.R., Miranda ALP, Silva KCM, Parrini SC, Barreiro EJ., Synthesis and evaluation of analgesic, antiinflammatory and antiplatelet properties of new 2-pyridylarylhydrazone derivatives, Eur. J. Med. Chem., 33:189-199 (1998).

Trost, B.M. and Frederiksen MU., Palladium-Catalyzed Asymmetric Allylation of Prochiral Nucleophiles:Synthesis of 3-Allyl-3-Aryl Oxindoles, Angew. Chem. Int. Ed. Engl., 44:308-310 (2005).

Varma, M., Pandeya SN, Singh KN, Stables JP., Anticonvulsant activity of Schiff bases of isatin derivatives, Acta Pharm., 54:49-56 (2004).

Varma, R.S., Khan IA., Potential Biologically Active Agents. X. Synthesis of 3-arylimino-2-indolinones, and their 1-methyl- and 1-morpholino/piperidinomethyl derivatives as excystment and cysticidal agents against Schizopyrenus russelli, Pol. J. Pharmacol. Pharm., 29:549-594 (1977).

Varma, R.S., Nobles WL., Antiviral, antibacterial, and antifungal activities of isatin N-Mannich bases, J. Pharm. Sci., 64:881-882 (1975).

Varma, R.S., Nobles WL., Synthesis and antiviral and antibacterial activity of certain N-dialkylaminomethylisatin betathiosemicarbazones, J. Med. Chem., 10:972-974 (1967).

Vicini, P., Zani F, Cozzini P, Doytchinova I., Hydrazones of 1,2-benzisothiazole hydrazides: synthesis, antimicrobial activity and QSAR investigations, Eur. J. Med. Chem., 37:553-564 (2002).

Wang, J.J., and Hu W-P J., Novel 3-Aza-Grob Fragmentation in Hydride Reduction of Ether-Protected Aromatic Lactams, J. Org. Chem., 64:5725-5727 (1999).

Yoshida, M., Asano M, Omichi H, Hayashi Y, Yamaguchi I, Matsudalnt K. Study of biodegradable copoly(l-lactic acid/glycolic acid) formulations with controlled release of Z-100 for application in radiation therapy, Int. J. Pharm. 115:61-67 (1995).

Zhou, L., Liu Y, Zhang W, Wei P, Huang C, Pei J, Yuan Y, Lai L. Isatin Compounds as Noncovalent SARS Coronavirus 3C-like Proteasa Inhibitors, J. Med. Chem., 49:3440-3443 (2006).

\* cited by examiner (A)

(B)

(A)

(B)

(A)

4 h treatment, A2058 melanoma (B)

(A)

A2058 melanoma cells (B)

DU145 prostate cancer cell

ISATIN DERIVATIVES, PHARMACEUTICAL COMPOSITIONS THEREOF, AND METHODS OF USE THEREOF

CROSS REFERENCE TO RELATED APPLICATIONS

This application claims the benefit of U.S. Provisional Patent Application No. 61/602,874, filed Feb. 24, 2012, which is incorporated herein by reference as if fully set forth herein.

BACKGROUND

Isatin (1H-indoline-2,3-dione) is an endogenous indole found in the mammalian brain, peripheral tissues, and body fluids. It has been widely used in synthesis of a large variety of heterocyclic compounds, such as indoles and quinolines. Recently, isatin has also exhibited many neurophysiological and neuropharmacological effects.[1] It is a versatile compound with a diversity of effects including antibacterial,[2-7] anticonvulsant,[8-11] antifungal,[5,7,12-15] antiviral,[10,17-19] anti-HIV,[20-22] antiprotozoal,[23-24] antihelminthic,[25-26] anti-TB,[27-35] anticancer,[36] antimycobacterial,[37] antimalarial[38-40] and anti-inflammatory activities.[41-42]

Various isatin derivatives have been developed to show various bioactivities, e.g. anti-tubercular,[43] and anti-viral.[44]

Thus, there is a need to develop novel isatin derivatives for various bioactivities, e.g. anti-cancer treatments.

SUMMARY OF THE INVENTION

One aspect of the invention relates to novel isatin derivative compounds.

Another aspect of the invention relates to a pharmaceutical composition comprising a therapeutically effective amount of at least one isatin derivative compound disclosed herein.

Another aspect of the invention relates to a method of treating a cancer or a tumor in a subject comprising administering to the subject a therapeutically effective amount of at least one isatin derivative compound disclosed herein or a pharmaceutical composition thereof as disclosed herein.

Another aspect of the invention relates to a method of treating a condition in a subject that can be regulated by the activation of one or more proteins (e.g. EGFR, Erk1/2, Her2/Neu, Jak2, Src, Stat3, Akt, Cyclin B1, and Cdc25C) comprising administering to the subject a therapeutically effective amount of at least one isatin derivative compound disclosed herein or a pharmaceutical composition thereof as disclosed herein.

Another aspect of the invention relates to a method of treating a condition in a subject that can be regulated by the disruption of microtubule formations in a subject comprising administering to the subject a therapeutically effective amount of at least one isatin derivative compound disclosed herein or a pharmaceutical composition thereof as disclosed herein.

BRIEF DESCRIPTIONS OF DRAWINGS

FIG. 1: Effects of Compounds 1~6 on DU145 prostate cancer cells.

Figure 2:
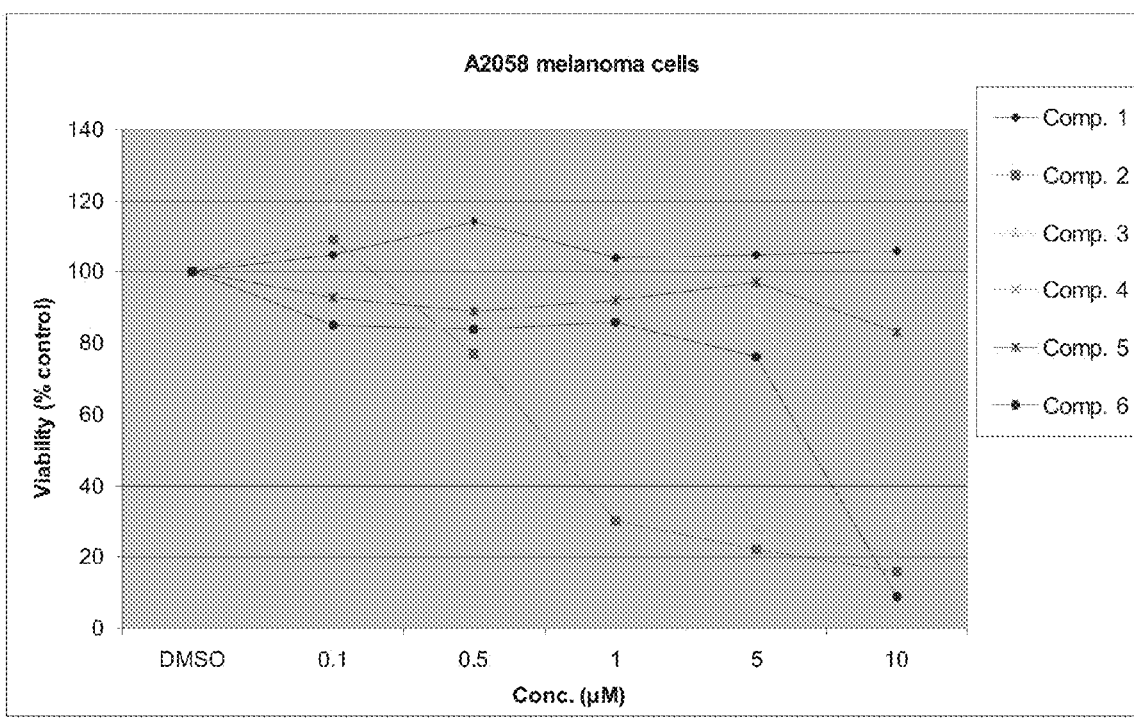

FIG. 2: Effects of Compounds 1~6 on A2058 melanoma cells.

Figure 3:
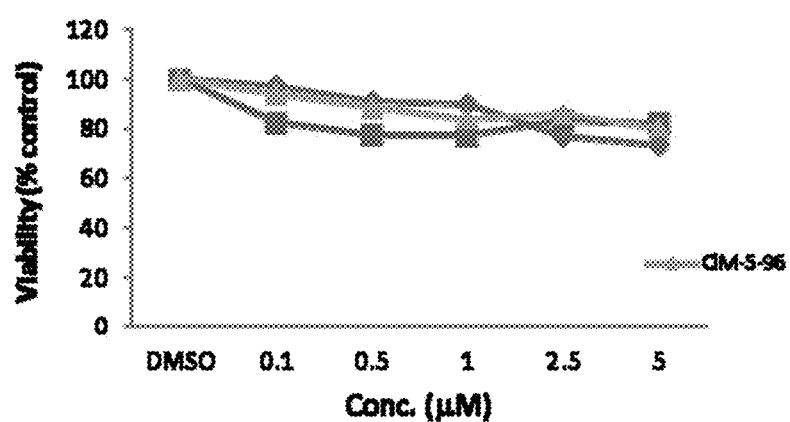

FIG. 3: Effects of Compound 17 on DU145 prostate cancer cells.

Figure 4:
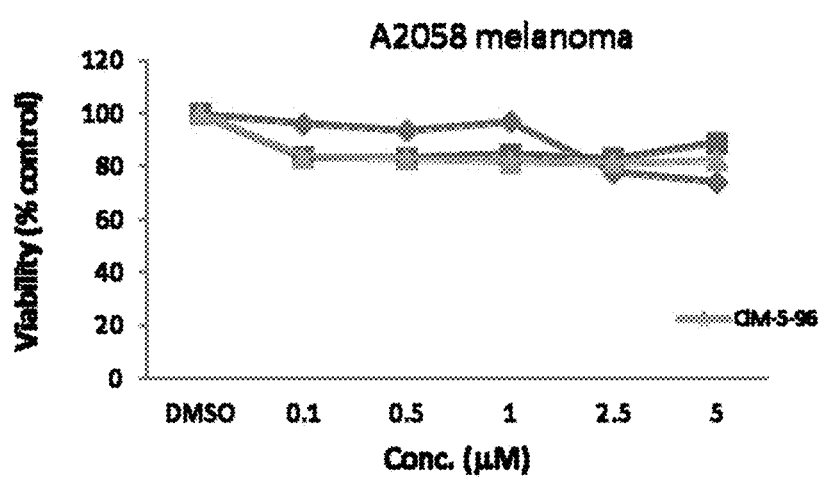

FIG. 4: Effects of Compound 17 on A2058 melanoma cells.

Figure 5:
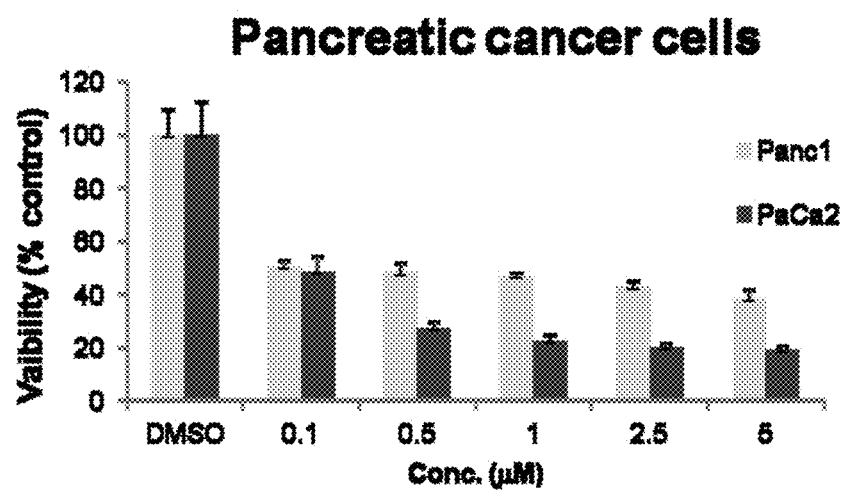

FIG. 5: Effects of Compound 22 on Panc 1 and PaCa2 pancreatic cancer cells.

Figure 6:
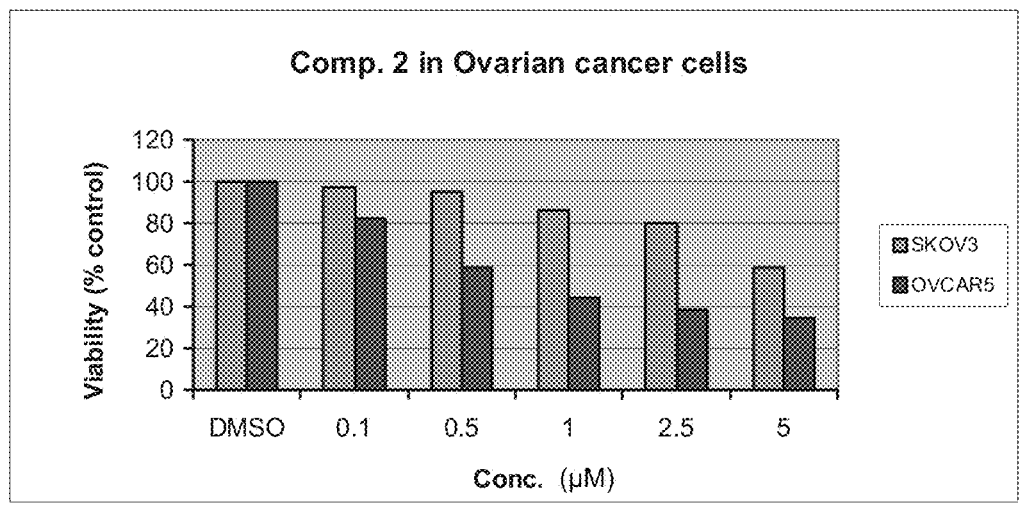

FIG. 6: Effects of Compound 2 on OVCAR5 and SKOV3 ovarian cancer cells.

Figure 7:
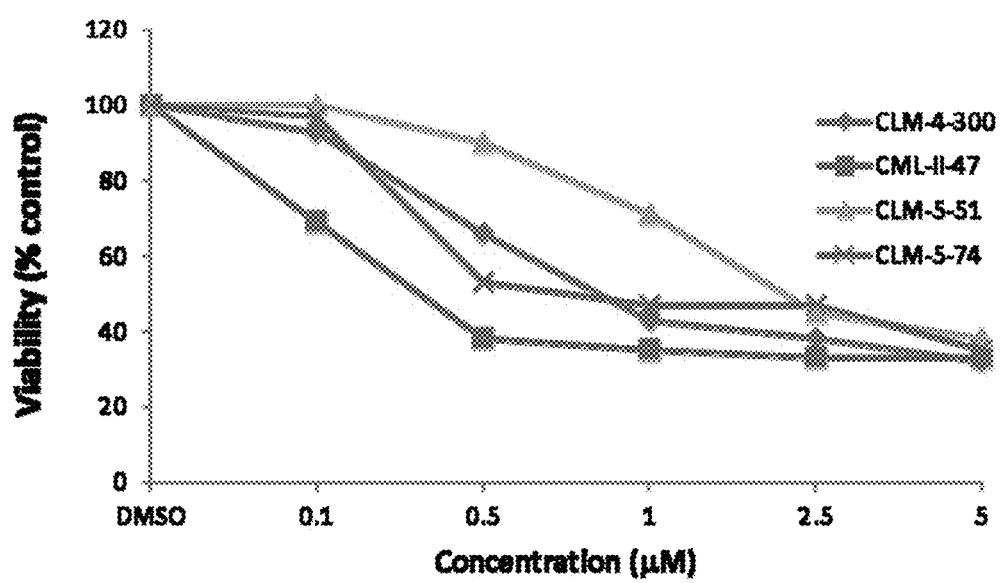

FIG. 7: Effects of Compounds 9, 12, 16 and 22 on OVCAR5 ovarian cancer cells.

Figure 8:
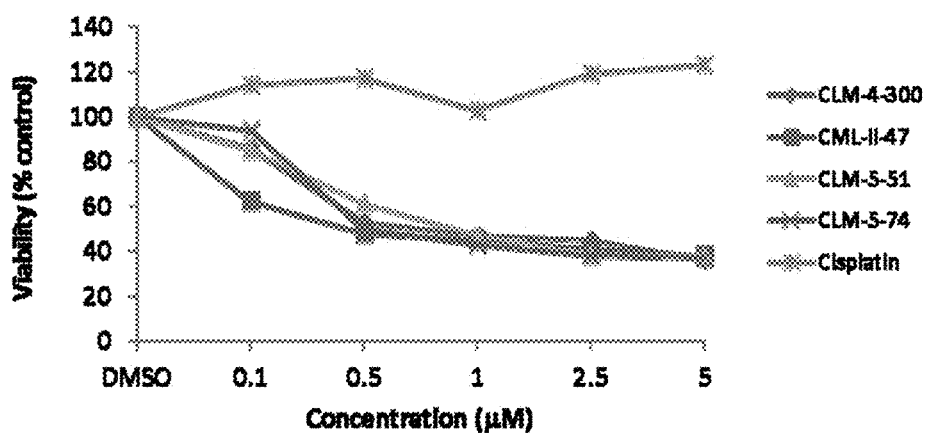
Figure 8:
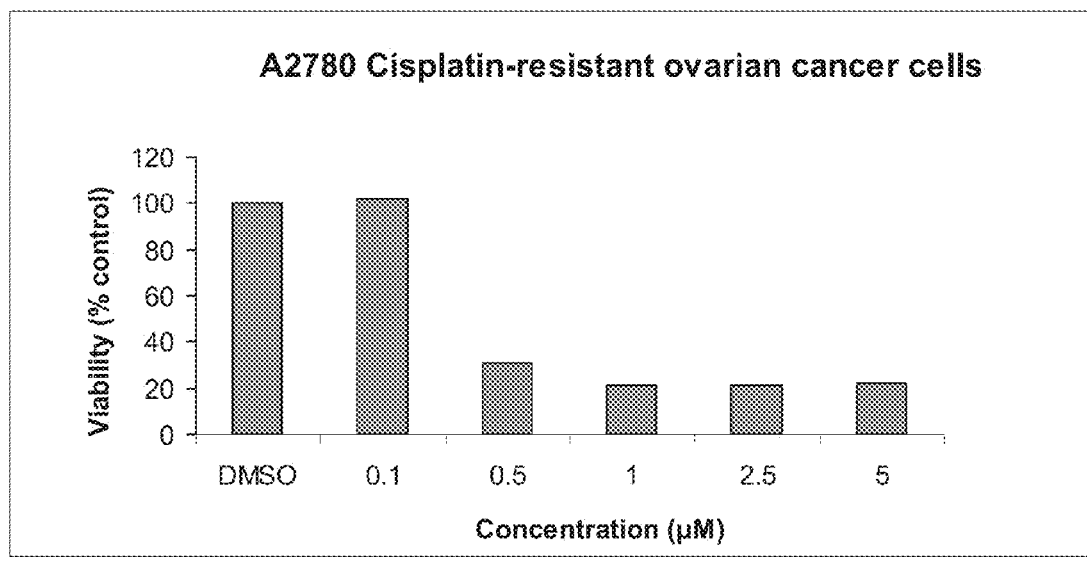

FIG. 8: Effects of isatin derivatives on A2780 cisplatin-resistant ovarian cancer cells. (A) Effects of Compounds 9, 12, 16 and 22 on A2780 cisplatin-resistant ovarian cancer cells; (B) Effects of Compound 9 on A2780 cisplatin-resistant ovarian cancer cells.

Figure 9:
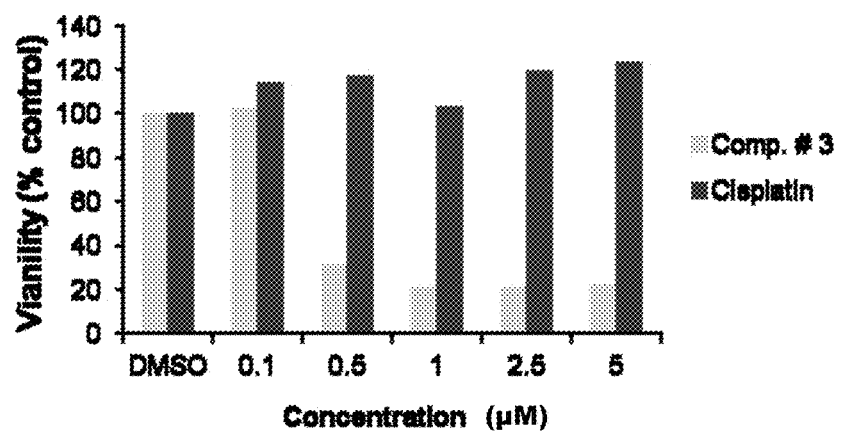

FIG. 9: Effects of Compound 9 and cisplatin on A2780 cisplatin-resistant ovarian cancer cells.

Figure 10:
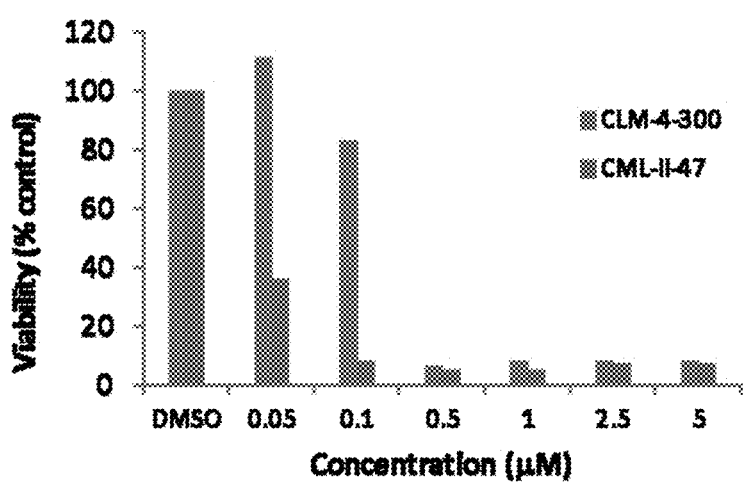

FIG. 10: Effects of Compounds 9 and 22 on OCI-Ly3 non-Hodgkin's B cell Lymphoma cells.

Figure 11:
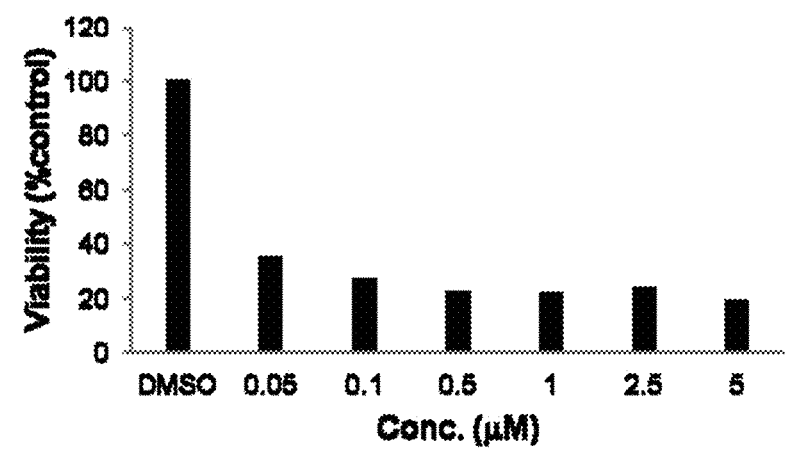
Figure 11:
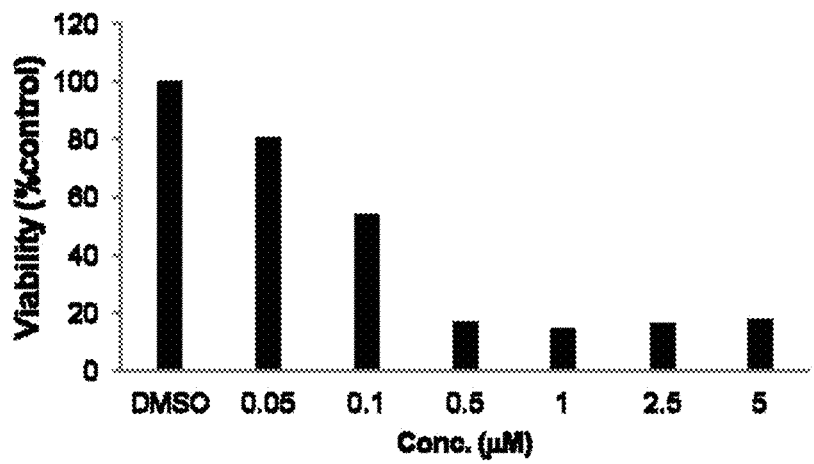

FIG. 11: Effects of Compound 22 on lymphoma cells. (A) Effects of Compound 22 on Daudi B cell Burkitt Lymphoma cells; and (B) Effects of Compound 22 on Anaplastic Large T cell Lymphoma cells.

Figure 12:
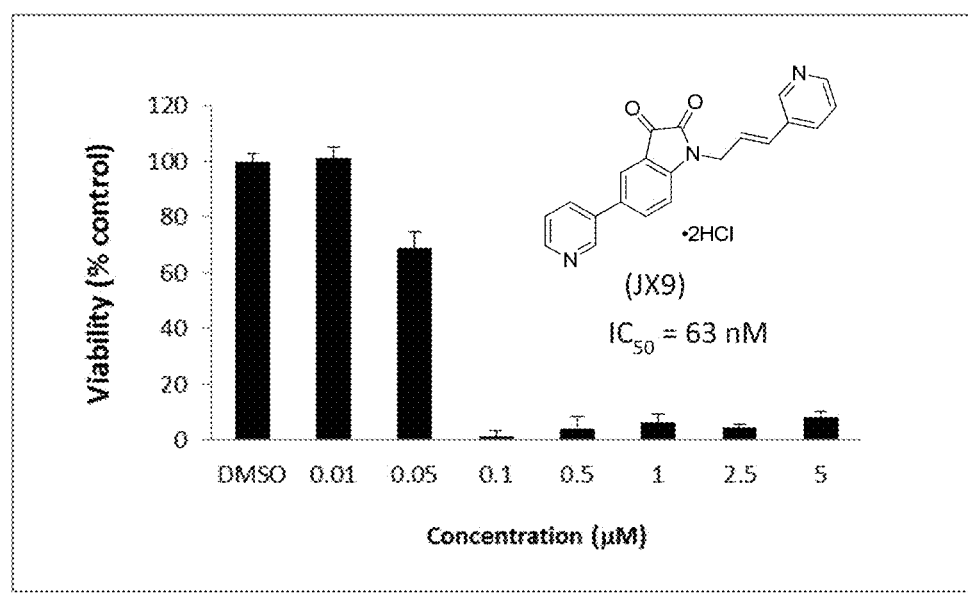

FIG. 12: Effects of Compound 109 on Ly-3 lymphoma cells.

Figure 13:
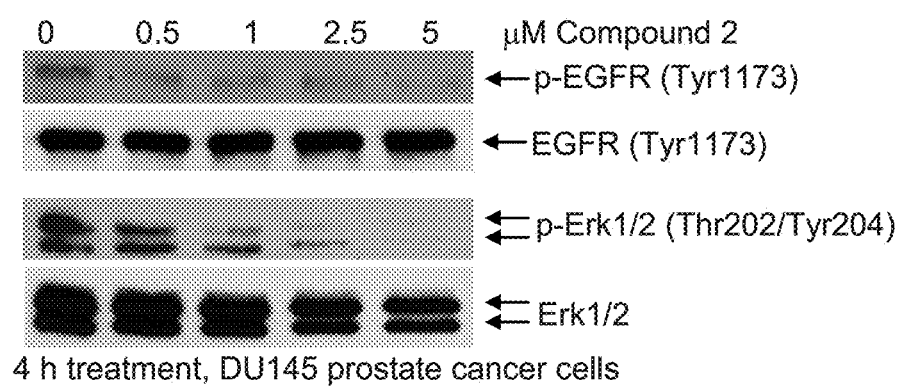

FIG. 13: Cellular effects of Compound 2 on DU145 prostate cancer cells (Concentration dependent manner).

Figure 14:
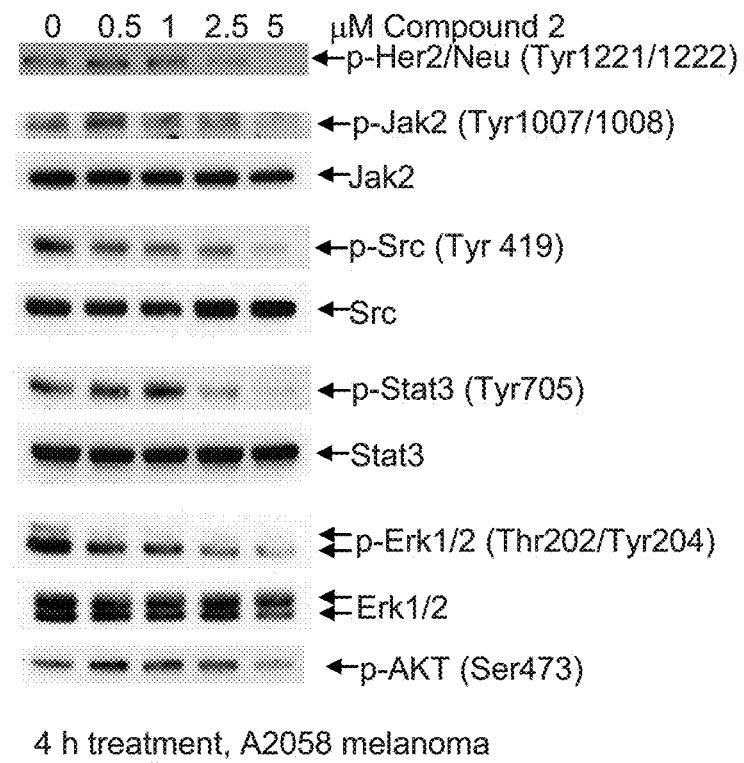
Figure 14:
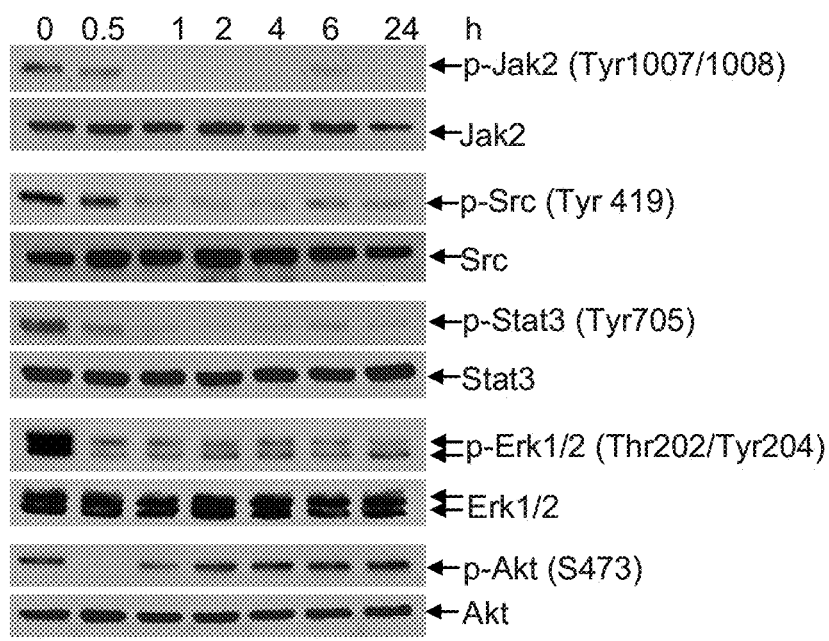

FIG. 14: Cellular effects of Compound 2 on A2058 melanoma (A) Concentration dependent manner and (B) Time dependent manner at a concentration of 5 μM.

Figure 15:
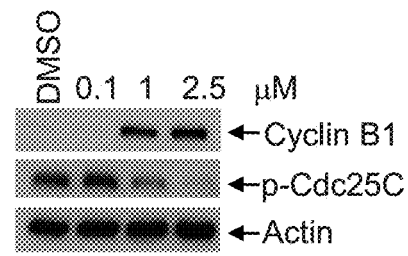
Figure 15:
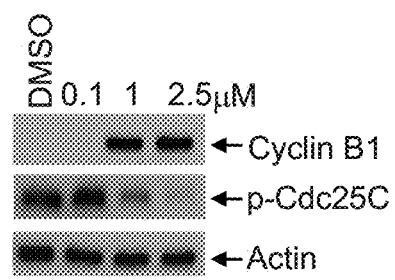

FIG. 15: Effects of Compound 22 on cell cycle of (A) DU145 prostate cancer cells and (B) A2058 melanoma cells.

Figure 16:
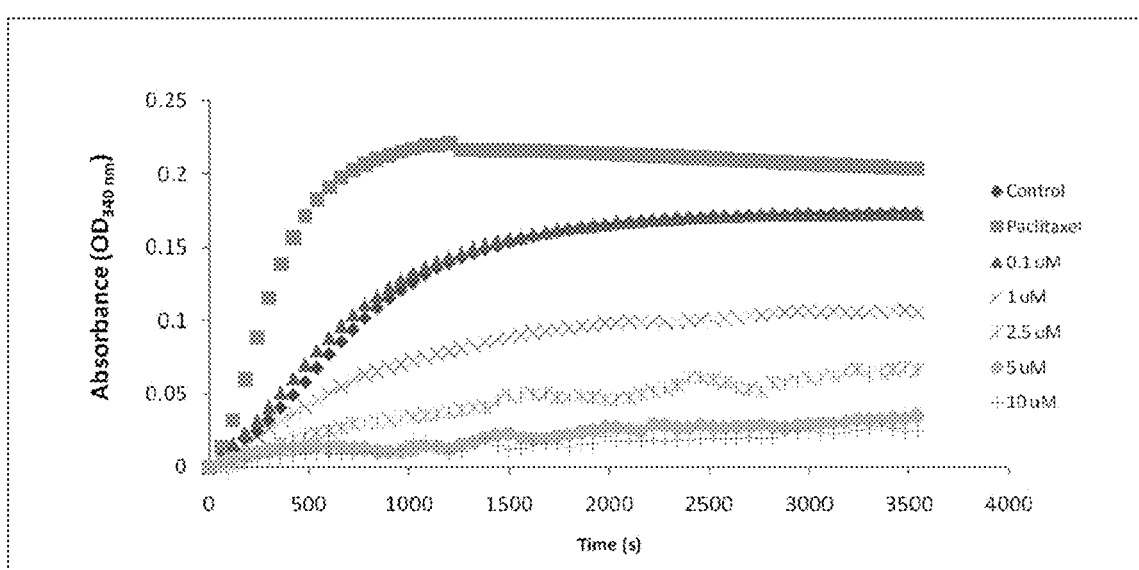

FIG. 16: Inhibition of microtubule formation by Compound 22 using in vitro tubulin polymerization assay.

Figure 17:
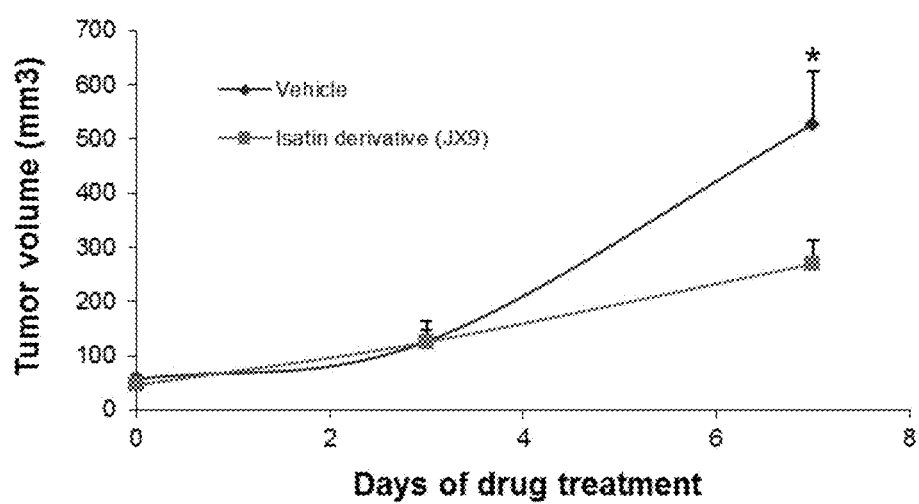

FIG. 17: Efficacy of Compound 109 on Ly-3 lymphoma SQ xenografts.

DETAILED DESCRIPTION OF THE INVENTION

I. Isatin Derivatives

One aspect of the invention relates to isatin derivatives comprising a structure of Structure I:

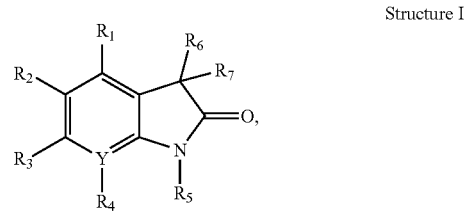

Structure I and the pharmaceutically acceptable solvates, salts and stereoisomers thereof, including mixtures thereof in all ratios wherein:

Y is C or N; preferably C;

$R_1$, $R_2$, $R_3$, and $R_4$ are independently selected from the group consisting of H, halogen (e.g. F, Cl, Br or I), alkyl, aryl, and heteroaryl;

$R_1$ is preferably selected from the group consisting of H, halogen, and heteroaryl; more preferably is H or halogen; more preferably is H or Br;

$R_2$ is preferably selected from the group consisting of halogen, alkyl, aryl, and heteroaryl; the heteroaryl group preferably comprises one or more atoms selected from the group consisting of N, O and S;

and optionally substituted with one or more substituents include, without limitation, halogen (e.g. F, Cl, Br, and I), and $NO_2$, more preferably F and $NO_2$; the preferred examples of $R_2$ includes, without limitation, I, methyl, propyl, isopropyl, phenyl, nitrophenyl, pyridinyl, pyrimidinyl, thiophenyl, furanyl, and fluoro pyridinyl;

$R_3$ is preferably selected from the group consisting of H, aryl, and halogen; and more preferably H;

$R_4$ is preferably selected from the group consisting of H, aryl, and halogen; and most preferably H;

$R_5$ is selected from the group consisting of H, halogen, $R_{50}$, $R_{50}$—$R_{51}$, $R_{50}$—$N(R_{52})$—$R_{51}$, —O—$R_{50}$—$R_{51}$, $R_{50}$—OH, $R_{50}$—O—$R_{51}$, and $R_{50}$—O—$R_{51}$—OH; and preferably selected from the group consisting of $R_{50}$, $R_{50}$—OH, $R_{50}$—$R_{51}$, and $R_{50}$—O—$R_{51}$—OH;

$R_{50}$ is selected from the group consisting of alkyl, alkenyl, aryl, and heteroaryl; preferably selected from the group consisting of alkyl, and alkenyl; the preferred examples of $R_{50}$ include, without limitation, C1~C6 alkyl, C2~C6 alkenyl, methyl, ethyl, propyl, butyl, and —C—C=C—;

$R_{51}$ is selected from the group consisting of alkyl, alkenyl, aryl, heteroaryl, and —$R_{50}$—$Si(R_{50})_3$, each $R_{50}$ group can be the same or different, preferably independently selected from the group consisting of alkyl, aryl, and heteroaryl, optionally substituted with one or more substituents selected from the group consisting of aryl (e.g. phenyl), alkyl, heteroaryl (e.g. pyridinyl, pyrimidinyl, thiophenyl, furanyl) and halogen (e.g. F, Cl, Br and I); the preferred examples of $R_{51}$ include, without limitation, phenyl, and heteroaryl groups comprising one or more atoms selected from the group consisting of N, O and S (e.g. pyridinyl, pyrimidinyl, thiophenyl, furanyl), optionally substituted with one or more substituents includes, without limitation, F, Cl, Br, I, and pyridinyl;

$R_{52}$ is selected from the group consisting of hydrogen and alkyl; and $R_6$ and $R_7$ taken together is =Z, or separately are independently selected from the group consisting of H, and OH;

Z is selected from the group consisting of O, NH, and N—$OR_z$;

$R_z$ is selected from the group consisting of H, alkyl, alkenyl, aryl, and heteroaryl; and $R_6$ and $R_7$ are preferably taken together to be =O.

As used herein, the term "solvate" refers to a complex of variable stoichiometry formed by a solute (in this invention, an isatin derivative comprising a structure of Structure I or a salt thereof) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compounds according to the invention.

The invention includes the pharmaceutically acceptable salts of all the compounds described herein. The salts include but are not limited to the following acids and bases. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

As used herein, the term "substituted" refers to substitution with one or more substituents.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, mixtures of enantiomers, as well as purified stereoisomers, purified enantiomers, or stereoisomerically enriched mixtures, enantiomerically enriched mixtures. Also included within the scope of the invention are the individual isomers of the compounds represented by Structure I above as well as any wholly or partially equilibrated mixtures thereof. The invention also covers the individual isomers of the compounds represented by Structure I above as mixtures with isomers thereof in which one or more chiral centers are inverted. Also, it is understood that all tautomers and mixtures of tautomers of the compounds of Structure I are included within the scope of the compounds of Structure I and preferably the structures corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent. The diastereomer resolution can also be carried out by standard purification processes, such as, for example, chromatography or fractional crystallization.

It is also possible to obtain optically active compounds comprising Structure I by the methods described above by using starting materials which are already optically active.

As used herein, the term "alkyl" refers to a straight or branched chain hydrocarbon having from one to twenty carbon atoms, optionally substituted with one or more substituents selected from the group consisting of C1~C6 alkyl, C1~C6 alkoxy, oxo, hydroxy, mercapto, amino optionally substituted by alkyl and/or aryl and/or heteroaryl, carboxy, carbamoyl optionally substituted by alkyl and/or aryl and/or heteroaryl, nitro, cyano, halogen, or C1~C6 perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "C1~C6 alkyl" refers to an alkyl group as defined above containing at least 1, and at most 6, carbon atoms. Examples of branched or straight chained "C1~C6 alkyl" groups include, but are not limited to, methyl, ethyl, n-propyl, isopropyl, isobutyl, n-butyl, t-butyl, n-pentyl, isopentyl and hexyl.

As used herein, the term "alkenyl" refers to an alkyl group as defined above further comprising one or more carbon-carbon double bond(s).

As used herein, the term "cycloalkyl" refers to a non-aromatic cyclic hydrocarbon ring having from three to seven carbon atoms and which optionally includes an alkyl linker through which it may be attached, preferably a C1~C6 alkyl linker as defined above. Such a ring may be optionally fused to one or more other "heterocyclic" ring(s) or cycloalkyl ring(s). Exemplary "cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a three to twelve-membered heterocyclic ring containing one or more heteroatomic substitutions on the ring selected from S, O or N, and optionally further substituted with one or more substituents selected from the group consisting of C1~C6 alkyl, C1~C6 haloalkyl, C1~C6 alkoxy, oxo, hydroxy, mercapto, amino optionally substituted by one or more alkyl, carboxy, carbamoyl optionally substituted by one or more alkyl, nitro, cyano, halogen, or C1~C6 perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, moieties derived from tetrahydrofuran, pyran, 1,4-dioxane, 1,3-dioxane, pyrrolidine, piperidine, morpholine, tetrahydrothiopyran, tetrahydrothiophene, and the like.

As used herein, the term "halogen" or "hal" refers to fluorine (F), chlorine (Cl), bromine (Br) or iodine (I).

As used herein, the term "aryl" refers to a benzene ring optionally substituted with one or more substituents, or to an optionally substituted benzene ring system fused to one or more benzene rings each optionally substituted with one or more substituents, e.g., anthracene, phenanthrene, or napthalene ring systems. Exemplary optional substituents include C1~C6 alkyl, C1~C6 alkoxy, oxo, hydroxy, mercapto, amino optionally substituted by alkyl and/or aryl and/or heteroaryl, carboxy, carbamoyl optionally substituted by alkyl and/or aryl and/or heteroaryl, acyl, aroyl, heteroaroyl, acyloxy, aroyloxy, heteroaroyloxy, alkoxycarbonyl, nitro, cyano, halogen, C1~C6 perfluoroalkyl, heteroaryl, or aryl. Examples of "aryl" groups include, but are not limited to phenyl, 2-naphthyl, 1-naphthyl, biphenyl, as well as substituted derivatives thereof.

As used herein, the term "heteroaryl" refers to a monocyclic five to seven-membered aromatic ring, or to a fused bicyclic aromatic ring system comprising two of such monocyclic five to seven-membered aromatic rings. These heteroaryl rings contain one or more nitrogen, sulfur and/or oxygen heteroatoms, where N-oxides and sulfur oxides and dioxides are permissible heteroatom substitutions and may be optionally substituted with up to three members selected from a group consisting of C1~C6 alkyl, C1~C6 haloalkyl, C1~C6 alkoxy, oxo, hydroxy, mercapto, amino optionally substituted by alkyl and/or aryl and/or heteroaryl, carboxy, carbamoyl optionally substituted by alkyl and/or aryl and/or heteroaryl, acyl, aroyl, heteroaroyl, acyloxy, aroyloxy, heteroaroyloxy, alkoxycarbonyl, nitro, cyano, halogen, C1~C6 perfluoroalkyl, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted derivatives thereof.

As used herein, the term "aralkyl" refers to an alkyl group as defined above substituted with at least one aryl group.

As used herein, the term "C1~C6 haloalkyl" refers to an alkyl group as defined above containing at least 1, and at most 6, carbon atoms substituted with at least one halogen, halogen being as defined herein. Examples of branched or straight chained "C1~C6 haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "alkoxy" refers to an alkyl group as defined above further comprising at least one oxygen substitution, e.g. $R_aO—$, wherein $R_a$ is alkyl as defined above. The term "C1~C6 alkoxy" refers to an alkoxy group as defined herein wherein the alkyl moiety contains at least 1 and at most 6 carbon atoms. Exemplary C1~C6 alkoxy groups useful in the invention include, but are not limited to methoxy, ethoxy, n-propoxy, isopropoxy, n-butoxy and t-butoxy.

As used herein, the term "cyanoalkyl" refers to an alkyl group as defined above further substituted with a cyano group. Exemplary "cyanoalkyl" groups useful in the invention include, but are not limited to, cyanomethyl, cyanoethyl and cyanoisopropyl.

As used herein, the term "carbamoyl" refers to the group $C(O)NH_2$.

As used herein, the term "acyl" refers to the group $R_AC(O)—$, where $R_A$ is alkyl, cycloalkyl or heterocyclyl as defined herein.

As used herein, the term "aroyl" refers to the group $R_BC(O)—$, where $R_B$ is aryl as defined herein.

As used herein, the term "heteroaroyl" refers to the group $R_CC(O)—$, where $R_D$ is heteroaryl as defined herein.

As used herein, the term "alkoxycarbonyl" refers to the group $R_DOC(O)—$, where $R_D$ is alkyl as defined herein.

As used herein, the term "acyloxy" refers to the group $R_EC(O)O$, where $R_E$ is alkyl, cycloalkyl, or heterocyclyl as defined herein.

As used herein, the term "aroyloxy" refers to the group $R_FC(O)O—$, where $R_F$ is aryl as defined herein.

As used herein, the term "heteroaroyloxy" refers to the group $R_GC(O)O—$, where $R_G$ is heteroaryl as defined herein.

As used herein, the term "carbonyl" or "carbonyl moiety" refers to the group $C=O$.

As used herein, the term "amino," "amino group" or "amino moiety" refers to the group $NR_HR_H'$, wherein $R_H$ and $R_H'$, are preferably selected, independently from one another, from the group consisting of hydrogen, alkyl, haloalkyl, alkenyl, cycloalkyl, alkylenecycloalkyl, cyanoalkyl, aryl, aralkyl, heteroaryl, acyl and aroyl. If both $R_H$ and $R_H'$ are hydrogen, $NR_HR_H'$ is also referred to as "unsubstituted amino moiety" or "unsubstituted amino group." If $R_H$ and/or $R_H'$ are other than hydrogen, $NR_HR_H'$ is also referred to as "substituted amino moiety" or "substituted amino group."

As used herein, the terms "group," "residue" and "radical" or "groups," "residues" and "radicals" are usually used as synonyms, respectively, as it is common practice in the art.

As used herein, the term "optionally" means that the subsequently described event(s) may or may not occur, and includes both event(s), which occur, and events that do not occur.

Preferred examples of the isatin derivatives and pharmaceutically acceptable salts thereof include, without limitation, Compounds 1~17 and 19~34 listed in Table 1a and Compounds 101~123 listed in Table 1b.

TABLE 1a

Structures of Compounds 1~17 and 19~34

| Compound No. | Isatin derivative [COH names] | Structure |
|---|---|---|
| 1. | A7 | 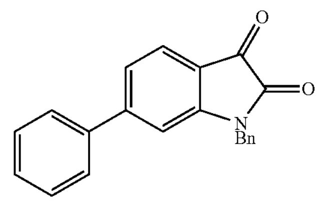 [SMILES: O=C1C(=O)N(Cc2ccccc2)c2cc(-c3ccccc3)ccc21] |
| 2. | A8 (also referred to as JME-1-93) | 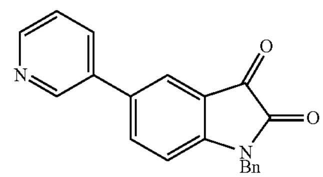 [SMILES: O=C1C(=O)N(Cc2ccccc2)c2ccc(-c3cccnc3)cc21] |
| 3. | A10 | 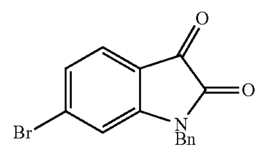 [SMILES: O=C1C(=O)N(Cc2ccccc2)c2cc(Br)ccc21] |
| 4. | B1 | 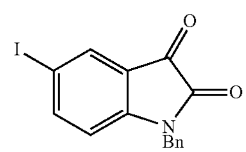 [SMILES: O=C1C(=O)N(Cc2ccccc2)c2ccc(I)cc21] |
| 5. | B2 | 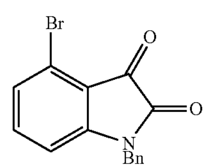 [SMILES: O=C1C(=O)N(Cc2ccccc2)c2cccc(Br)c21] |
| 6. | B3 | 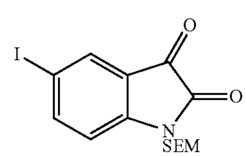 [SMILES: C[Si](C)(C)CCOCN1C(=O)C(=O)c2cc(I)ccc21] |
| 7. | CLM-4 292 | 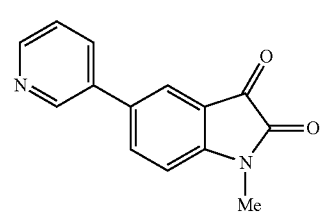 [SMILES: CN1C(=O)C(=O)c2cc(-c3cccnc3)ccc21] |

TABLE 1a-continued
Structures of Compounds 1~17 and 19~34
| Compound No. | Isatin derivative [COH names] | Structure |
|---|---|---|
| 8. | CLM-4 293 | 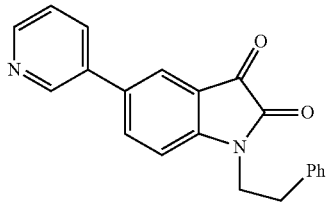 [SMILES: O=C1C(=O)N(CCc2ccccc2)c2ccc(-c3cccnc3)cc21] |
| 9. | CLM-4 300 | 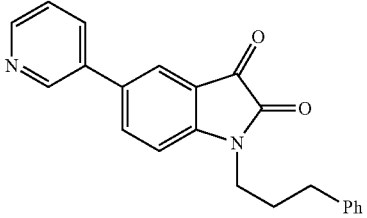 [SMILES: O=C1C(=O)N(CCCc2ccccc2)c2ccc(-c3cccnc3)cc21] |
| 10. | CLM-4 302 | 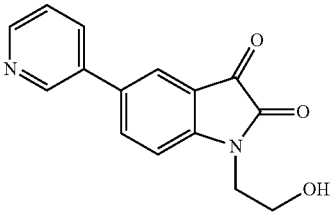 [SMILES: O=C1C(=O)N(CCO)c2ccc(-c3cccnc3)cc21] |
| 11. | CLM-5-12 | 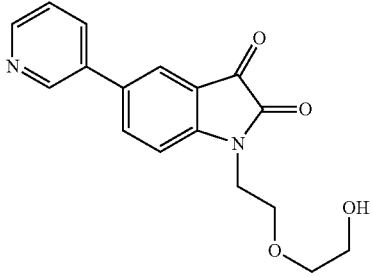 [SMILES: O=C1C(=O)N(CCOCCO)c2ccc(-c3cccnc3)cc21] |
| 12. | CLM-5-51 | 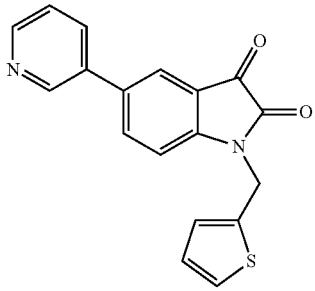 [SMILES: O=C1C(=O)N(Cc2cccs2)c2ccc(-c3cccnc3)cc21] |
| 13. | CLM-5-53 | 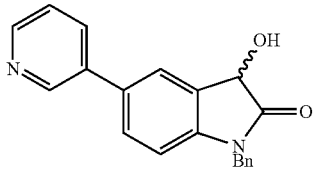 |

TABLE 1a-continued

Structures of Compounds 1~17 and 19~34

| Compound No. | Isatin derivative [COH names] | Structure |
|---|---|---|
| 14. | CLM-5-62 | 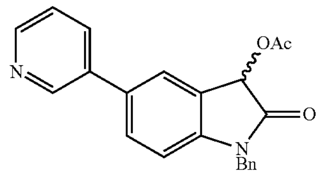 [SMILES: O=C1C(O)c2cc(-c3cccnc3)ccc2N1Cc1ccccc1] |
| 15. | CLM-5-70 | 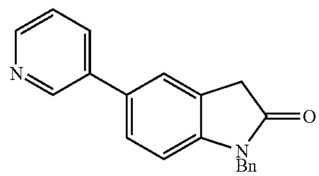 [SMILES: O=C1Cc2cc(-c3cccnc3)ccc2N1Cc1ccccc1] |
| 16. | CLM-5-74 | 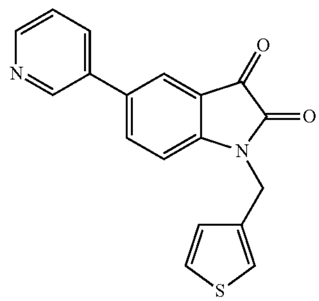 [SMILES: O=C1C(=O)N(Cc2ccsc2)c2ccc(-c3cccnc3)cc21] |
| 17. | CLM-5-96 | 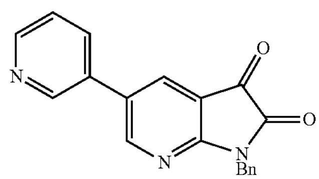 [SMILES: O=C1C(=O)N(Cc2ccccc2)c2ncc(-c3cccnc3)cc21] |
| 18. | CML-II-40 | 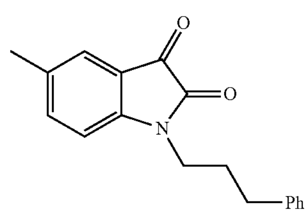 [SMILES: Cc1ccc2c(c1)C(=O)C(=O)N2CCCc1ccccc1] |
| 20. | CML-II-42 | 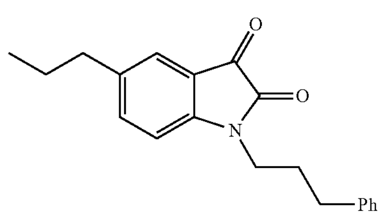 [SMILES: CCCc1ccc2c(c1)C(=O)C(=O)N2CCCc1ccccc1] |
| 21. | CML-II-43 | 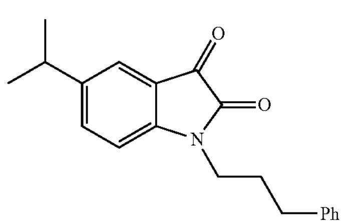 [SMILES: CC(C)c1ccc2c(c1)C(=O)C(=O)N2CCCc1ccccc1] |

TABLE 1a-continued

Structures of Compounds 1~17 and 19~34

| Compound No. | Isatin derivative [COH names] | Structure |
|---|---|---|
| 22. | CML-II-47 | 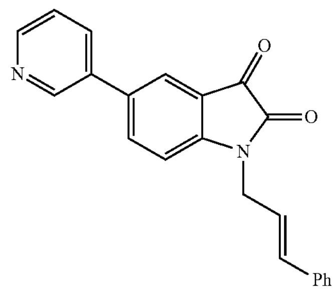 [SMILES: O=C1C(=O)N(C/C=C/c2ccccc2)c2ccc(-c3cccnc3)cc21] |
| 23. | CML-II-49 | 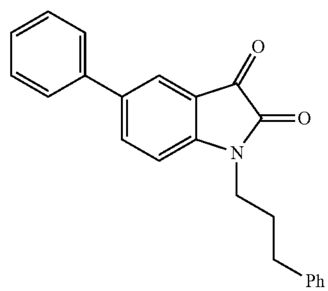 [SMILES: O=C1C(=O)N(CCCc2ccccc2)c2ccc(-c3ccccc3)cc21] |
| 24. | CML-II-54 | 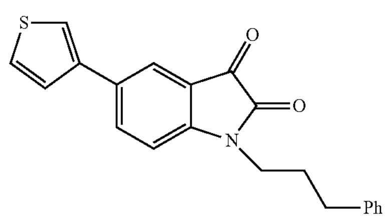 [SMILES: O=C1C(=O)N(CCCc2ccccc2)c2ccc(-c3ccsc3)cc21] |
| 25. | CML-II-57 | 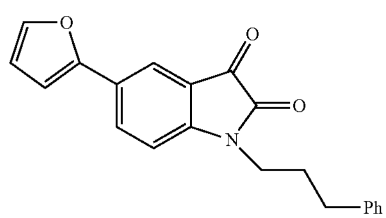 [SMILES: O=C1C(=O)N(CCCc2ccccc2)c2ccc(-c3ccco3)cc21] |
| 26. | JRS-I-30 | 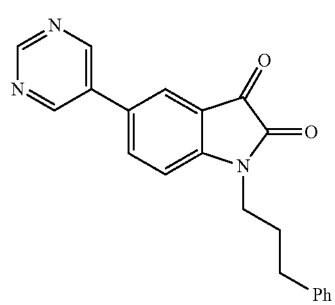 [SMILES: O=C1C(=O)N(CCCc2ccccc2)c2ccc(-c3cncnc3)cc21] |

TABLE 1a-continued

Structures of Compounds 1~17 and 19~34

| Compound No. | Isatin derivative [COH names] | Structure |
|---|---|---|
| 27. | JRS-I-33 | 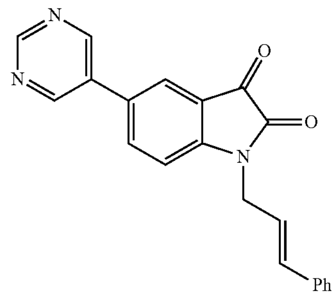 [SMILES: O=C1C(=O)N(C/C=C/c2ccccc2)c2ccc(-c3cncnc3)cc21] |
| 28. | JRS-I-35 | 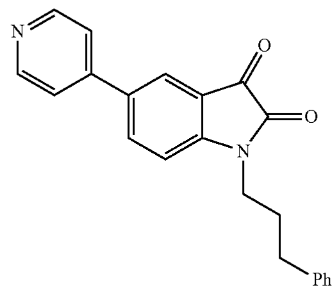 [SMILES: O=C1C(=O)N(CCCc2ccccc2)c2ccc(-c3ccncc3)cc21] |
| 29. | JRS-I-36 | 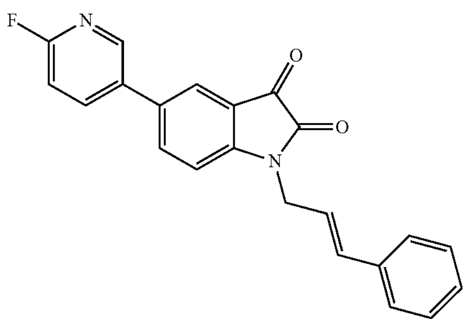 [SMILES: O=C1C(=O)N(C/C=C/c2ccccc2)c2ccc(-c3ccc(F)nc3)cc21] |
| 30. | JRS-I-41 | 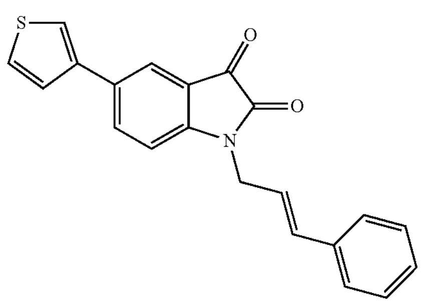 [SMILES: O=C1C(=O)N(C/C=C/c2ccccc2)c2ccc(-c3ccsc3)cc21] |
| 31. | JRS-I-43 | 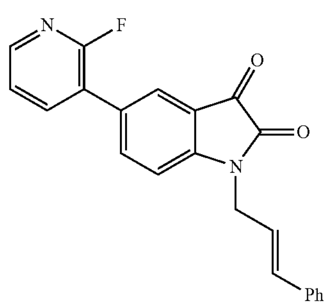 [SMILES: O=C1C(=O)N(C/C=C/c2ccccc2)c2ccc(-c3cccnc3F)cc21] |

TABLE 1a-continued

Structures of Compounds 1~17 and 19~34

| Compound No. | Isatin derivative [COH names] | Structure |
|---|---|---|
| 32. | JX-Istatin-1 | 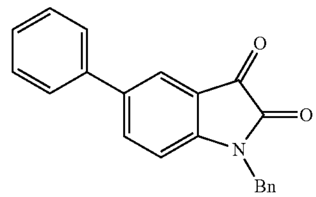 [SMILES: O=C1C(=O)N(Cc2ccccc2)c2ccc(-c3ccccc3)cc21] |
| 33. | JX-Istatin-2 | 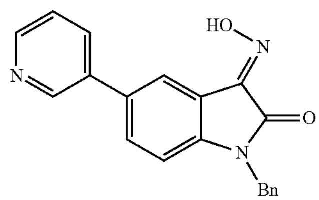 [SMILES: O=C1/C(=N/O)c2cc(-c3cccnc3)ccc2N1Cc1ccccc1] |
| 34. | JX-Istatin-3 | 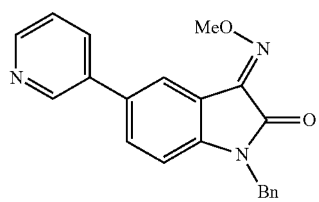 [SMILES: CO/N=C1/C(=O)N(Cc2ccccc2)c2ccc(-c3cccnc3)cc21] |

As used herein, "Bn" is benzyl group; and "SEM" is 2-(trimethylsilyl)ethoxymethyl group.

The more preferred examples of isatin derivatives include, without limitation, Compound 2, Compound 9, Compound 12, Compound 16, Compound 22, Compound 26, Compound 27, Compound 29, Compound 30, and Compound 31.

Preferred examples of the isatin derivatives that is water soluble include, without limitation, Compounds 101~123 listed in Table 1b:

TABLE 1b

Structures of Compounds 101~123

| Compound No. | Isatin derivative [COH names] | Structure |
|---|---|---|
| 101. | JX1 | 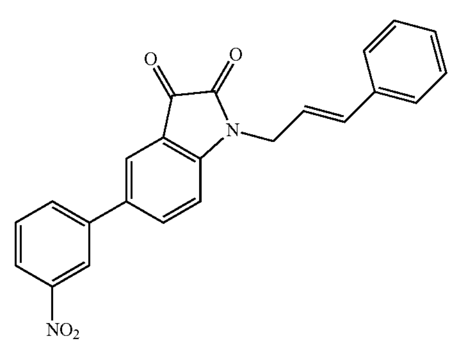 [SMILES: O=C1C(=O)N(C/C=C/c2ccccc2)c2ccc(-c3cccc([N+](=O)[O-])c3)cc21] |

TABLE 1b-continued
Structures of Compounds 101~123
| Compound No. | Isatin derivative [COH names] | Structure |
|---|---|---|
| 102. | JX2 | 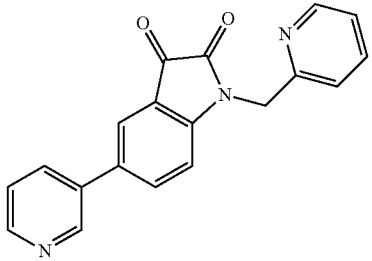 [SMILES: O=C1C(=O)N(Cc2ccccn2)c2ccc(-c3cccnc3)cc21] |
| 103. | JX3 | 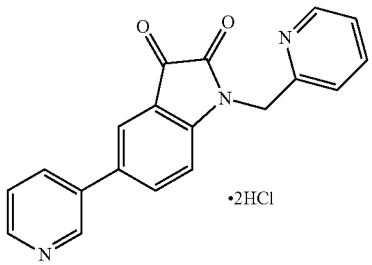 [SMILES: O=C1C(=O)N(Cc2ccccn2)c2ccc(-c3cccnc3)cc21] •2HCl |
| 104. | JX4 | 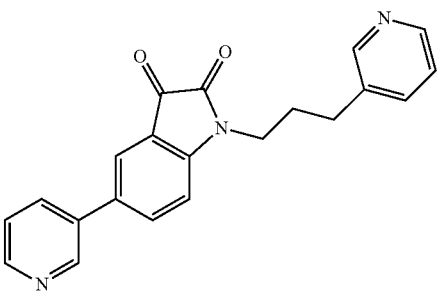 [SMILES: O=C1C(=O)N(CCCc2cccnc2)c2ccc(-c3cccnc3)cc21] |
| 105. | JX5 | 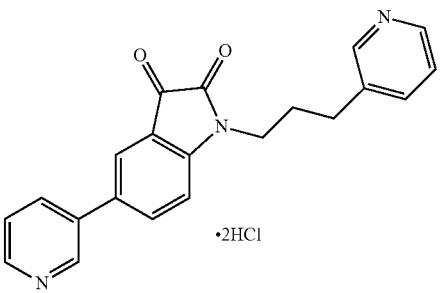 [SMILES: O=C1C(=O)N(CCCc2cccnc2)c2ccc(-c3cccnc3)cc21] •2HCl |
| 106. | JX6 | 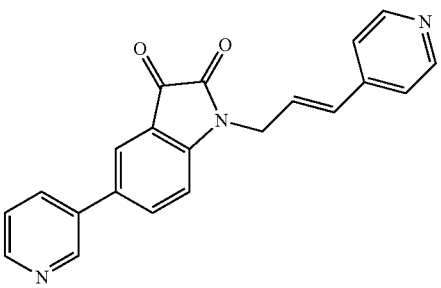 [SMILES: O=C1C(=O)N(C/C=C/c2ccncc2)c2ccc(-c3cccnc3)cc21] |

TABLE 1b-continued

Structures of Compounds 101~123

| Compound No. | Isatin derivative [COH names] | Structure |
|---|---|---|
| 107. | JX7 | (structure with 5-(pyridin-3-yl)isatin N-substituted with 3-(pyridin-4-yl)allyl group) ·2HCl |
| 108. | JX8 | (structure with 5-(pyridin-3-yl)isatin N-substituted with 3-(pyridin-3-yl)allyl group) |
| 109. | JX9 | (structure with 5-(pyridin-3-yl)isatin N-substituted with 3-(pyridin-3-yl)allyl group) ·2HCl |
| 110. | JX10 | (structure with 5-(pyridin-3-yl)isatin N-substituted with 3-(pyridin-2-yl)allyl group) |
| 111. | JX11 | (structure with 5-(pyridin-3-yl)isatin N-substituted with 3-(pyridin-2-yl)allyl group) ·2HCl |

TABLE 1b-continued
Structures of Compounds 101~123
| Compound No. | Isatin derivative [COH names] | Structure |
|---|---|---|
| 112. | JX12 | 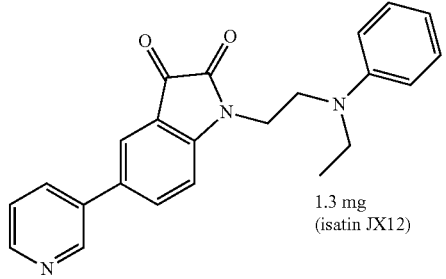 [SMILES: CCN(CCN1C(=O)C(=O)c2cc(-c3cccnc3)ccc21)c1ccccc1] 1.3 mg (isatin JX12) |
| 113. | JX13 | 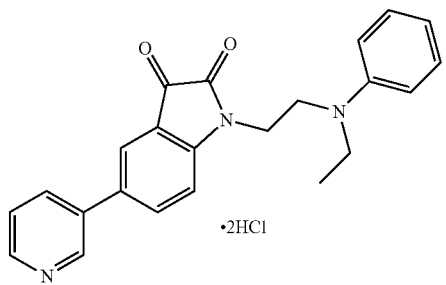 [SMILES: CCN(CCN1C(=O)C(=O)c2cc(-c3cccnc3)ccc21)c1ccccc1] •2HCl |
| 114. | JX14 | 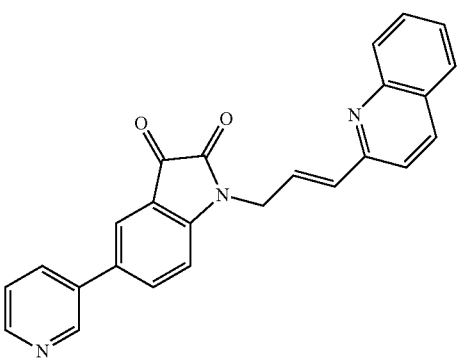 [SMILES: O=C1C(=O)N(C/C=C/c2ccc3ccccc3n2)c2ccc(-c3cccnc3)cc21] |
| 115. | JX15 | 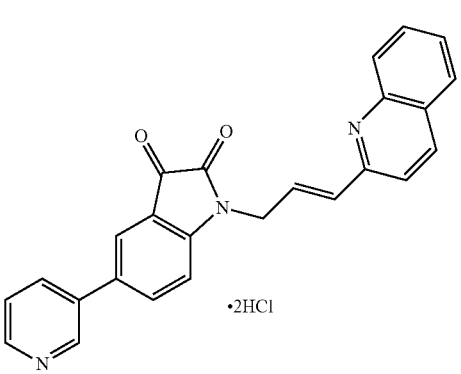 [SMILES: O=C1C(=O)N(C/C=C/c2ccc3ccccc3n2)c2ccc(-c3cccnc3)cc21] •2HCl |

TABLE 1b-continued

Structures of Compounds 101~123

| Compound No. | Isatin derivative [COH names] | Structure |
| --- | --- | --- |
| 116. | JX16 | 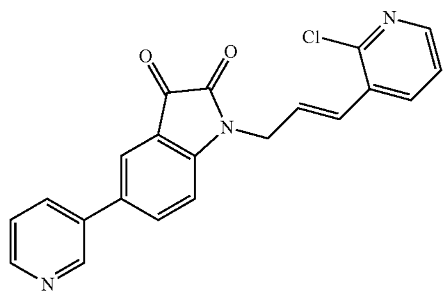 [SMILES: O=C1C(=O)N(C/C=C/c2cccnc2Cl)c2ccc(-c3cccnc3)cc21] |
| 117. | JX17 | 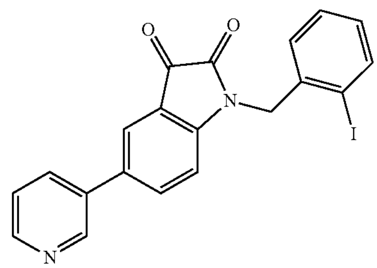 [SMILES: O=C1C(=O)N(Cc2ccccc2I)c2ccc(-c3cccnc3)cc21] |
| 118. | JX18 | 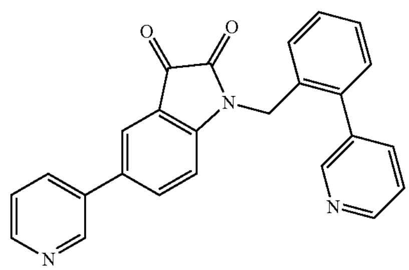 [SMILES: O=C1C(=O)N(Cc2ccccc2-c2cccnc2)c2ccc(-c3cccnc3)cc21] |
| 119. | JX19 | 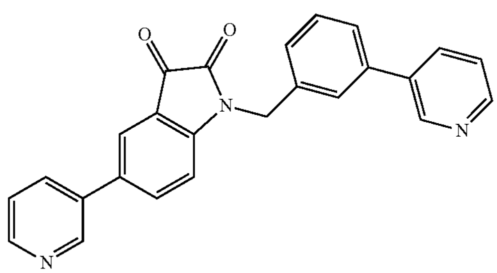 [SMILES: O=C1C(=O)N(Cc2cccc(-c3cccnc3)c2)c2ccc(-c3cccnc3)cc21] |
| 120. | JX20 | (·2HCl) |

TABLE 1b-continued

Structures of Compounds 101~123

| Compound No. | Isatin derivative [COH names] | Structure |
|---|---|---|
| 121. | JX21 | (structure) |
| 122. | JX22 | (structure) |
| 123. | JX23 | (structure) ·2HCl |

In certain embodiments, the more preferred examples of isatin derivatives include, without limitation, Compounds 101~111, Compounds 114~123. In certain embodiments, the more preferred examples of isatin derivatives include, without limitation, Compounds 104, 107~111, Compounds 114~116, and Compounds 121~123.

II. Pharmaceutical Compositions

Another aspect of the invention relates to a pharmaceutical composition comprising a therapeutically effective amount of at least one isatin derivative described herein. In certain embodiments, the pharmaceutical composition further comprises a pharmaceutically acceptable carrier.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance a normal physiological function. An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the isatin derivative is being used, the route of administration, and the size (body weight, body surface or organ size) and condition (the age and general health) of the subject. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

Pharmaceutically acceptable carrier is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body. Each carrier is "pharmaceutically acceptable" in the sense of being compatible with the other ingredients, e.g., the isatin derivatives described herein or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Pharmaceutically acceptable carriers are well known in the art and include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an active ingredient in these formulations can vary widely, and will be selected primarily based on fluid volumes, viscosities, body weight and the like in accordance with the particular mode of administration selected and the biological subject's needs. For example, the concentration can be 0.0001 to 100%, 0.001% to 50%, 0.01% to 30%, 0.1% to 20%, 1% to 10% wt.

A suitable pharmaceutically acceptable carrier may be selected taking into account the chosen mode of administration, and the physical and chemical properties of the compounds.

One skilled in the art will recognize that a pharmaceutical composition containing at least one isatin derivative disclosed herein can be administered to a subject by various routes including, without limitation, orally or parenterally, such as intravenously. The composition can be administered by injection or by intubation.

In one embodiment, the pharmaceutical carrier may be a liquid and the pharmaceutical composition would be in the form of a solution. In another embodiment, the pharmaceutically acceptable carrier is a solid and the pharmaceutical composition is in the form of a powder, tablet, pill, or capsules. In another embodiment, the pharmaceutical carrier is a gel and the pharmaceutical composition is in the form of a suppository or cream.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of at least one isatin derivative described herein the pharmaceutical composition may also include suitable diluents, preservatives, solubilizers, emulsifiers, adjuvant and/or carriers.

The pharmaceutical composition can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also recognized by those skilled in the art. See for example, PCT/US93/00829[48] that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides,[49-50] copolymers of L-glutamic acid and gamma ethyl-L-glutamate,[51] poly (2-hydroxyethyl-methacrylate),[52-53] ethylene vinyl acetate[52-53] or poly-D(−)-3-hydroxybutyric acid.[54] Sustained-release compositions also include liposomes, which can be prepared by any of several methods known in the art.[55-58]

In one embodiment, the present invention is directed to kits for producing a single-dose administration unit. The kits may each contain both a first container having dried components and a second container having a formulation comprising a pharmaceutically acceptable carrier (e.g. an aqueous formulation). Also included within the scope of this invention are kits containing single and multi-chambered pre-filled syringes (e.g., liquid syringes and lyosyringes).

III. Methods of Using Isatin Derivatives or a Pharmaceutical Composition Thereof.

Another aspect of the invention relates to a method of treating a cancer or tumor in a subject comprising administering to the subject a therapeutically effective amount of at least one isatin derivative disclosed herein or a pharmaceutical composition thereof.

Optimal dosages to be administered may be determined by those skilled in the art, and will vary with the particular compound in use, the strength of the preparation, the mode of administration, and the advancement of the disease condition. Additional factors depending on the particular subject being treated, includes, without limitation, subject age, weight, gender, diet, time of administration, time and frequency of administration, drug combination(s), reaction sensitivities, and response to therapy. Administration of the pharmaceutical composition may be effected continuously or intermittently. In any treatment regimen, the pharmaceutical composition may be administered to a patient either singly or in a cocktail containing two or more isatin derivatives, other therapeutic agents, compositions, or the like, including, but not limited to, tolerance-inducing agents, potentiators and side-effect relieving agents. All of these agents are administered in generally-accepted efficacious dose ranges such as those disclosed in the Physician's Desk Reference, 41st Ed., Publisher Edward R. Barnhart, N.J. (1987).[47] In certain embodiments, an appropriate dosage level will generally be about 0.001 to 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

The frequency of dosing will depend upon the pharmacokinetic parameters of the therapeutic agents in the pharmaceutical composition (e.g. an isatin derivative disclosed herein) used. Typically, a pharmaceutical composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. Long-acting pharmaceutical compositions may be administered every 3 to 4 days, every week, or biweekly depending on the half-life and clearance rate of the particular formulation.

Examples of the cancer or tumor treated in the method include, without limitation, prostate cancer, melanoma, pancreatic cancer, ovarian cancer, and lymphoma. The preferred cancer treated in the method disclosed herein include, without limitation, prostate cancer, melanoma, pancreatic cancer, ovarian cancer, and lymphoma.

In one embodiment, the cancer treated in the method is prostate cancer, and the isatin derivative is selected from the group consisting of Compounds 1~17, Compounds 19~34 and Compounds 101~123. In another embodiment, the cancer treated in the method is prostate cancer, and the isatin derivative is selected from the group consisting of Compounds 2, 4, 6~9, 12~13, 16, 22~32, 101~111, and 114~123. In another embodiment, the cancer treated in the method is prostate cancer, and the isatin derivative is selected from the group consisting of Compounds 2, 9, 12, 16, 22, 26, 27, 29~31, 104, 106~111, 116, and 121~123.

In another embodiment, the cancer treated in the method is melanoma, and the isatin derivative is selected from the group consisting of Compounds 1~17, Compounds 19~34, and Compounds 101~123. In another embodiment, the cancer treated in the method is melanoma, and the isatin derivative is selected from the group consisting of Compounds 2, 4, 7, 9, 12~13, 16, 22, 24~32, 101~111, and 114~123. In another embodiment, the cancer treated in the method is melanoma, and the isatin derivative is selected from the group consisting of Compounds 2, 9, 22, 26~27, 29, 31, 108~111, 114~116, and 121~123.

In another embodiment, the cancer treated in the method is pancreatic cancer, and the isatin derivative is selected from the group consisting of Compounds 2, and 22.

In another embodiment, the cancer treated in the method is ovarian cancer, and the isatin derivative is selected from the group consisting of Compounds 2, 9, 12, 16, and 22. In another embodiment, the cancer treated in the method is ovarian cancer that is resistant to cisplatin, and the isatin derivative is selected from the group consisting of Compounds 9, 12, and 22.

In another embodiment, the cancer treated in the method is lymphoma, and the isatin derivative is selected from the group consisting of Compounds 9, 22, and 109.

Another aspect of the invention relates to a method of treating a condition in a subject that can be regulated by the activation of one or more proteins comprising administering to the subject a therapeutically effective amount of at least one isatin derivative disclosed herein or a pharmaceutical composition thereof.

In one embodiment, examples of such proteins include, without limitation, EGFR (epidermal growth factor receptor), Erk1/2 (extracellular signal-regulated kinases), Her2/Neu (human epidermal growth factor receptor 2), Jak2 (Janus kinase 2), Src, Stat3 (Signal transducer and activator of transcription 3), Akt (also known as Protein Kinase B (PKB)), Cyclin B1, and Cdc25C (cell division cycle 25 homolog C).

In another embodiment, the condition treated is a cancer or tumor (e.g. melanoma). The one or more proteins are involved in one or more cancer cell signal transduction pathways. Antagonists of activation of signal proteins involved in these cell signal transduction pathways may have potentials for anti-cancer treatments. In certain embodiments, cancer cells treated with at least one isatin derivatives (e.g. Compound 2) disclosed herein showed less activation of certain signal proteins (e.g. EGFR, Erk1/2, Her2/Neu, Jak2, Src, Stat3, and Akt (PKB).

In another embodiments, the condition treated is a cancer or tumor (e.g. melanoma and prostate cancer. Cancer cells treated with at least one isatin derivatives (e.g. Compound 22) disclosed herein showed a concentration-associated increase of Cyclin B1 and concentration-associated decrease of phosphorylated Cdc25C.

Another aspect of the invention relates to a method of treating a condition in a subject that can be regulated by the disruption of microtubule formations comprising administering to the subject a therapeutically effective amount of at least one isatin derivative disclosed herein or a pharmaceutical composition thereof.

In one embodiments, the condition treated is a cancer or a tumor. In certain embodiments, the at least one isatin derivative is Compound 22.

In another embodiment, the condition treated is rheumatic complaint.

EXAMPLES

Example 1. Preparation of Isatin Derivatives

Materials and Methods.

Unless stated otherwise, all reactions were conducted in flame-dried glassware under an atmosphere of nitrogen using anhydrous solvents (either freshly distilled or passed through activated alumina columns). All commercially obtained reagents were used as received. Elevated reaction temperatures were regulated using a temperature modulator, whereas prolonged low temperature reactions were carried out using a cryoscopic bath. Unless otherwise noted, reactions were performed at room temperature (rt, approximately 23° C.). Thin layer chromatography (TLC) was conducted with pre-coated silica gel plates (0.25 mm) and visualized using a combination of UV, anisaldehyde, ceric ammonium molybdate, iodine on silica, and potassium permanganate staining. Silica gel (particle size 0.040-0.063 mm) was used for flash chromatography. $^1$H NMR spectra were recorded at 400 and 500 MHz, and are reported relative to deuterated solvent signals. Data for $^1$H NMR spectra are reported as follows: chemical shift (δ ppm), multiplicity, coupling constant (Hz), and integration. $^{13}$C NMR spectra were recorded on spectrometers at 100 and 125 MHz, and are reported in terms of chemical shift. Hydrogen multiplicity assignments were made using DEPT and HMQC two-dimensional NMR. IR spectra were recorded by depositing the sample on the probe of an in situ FTIR instrument, and are reported in terms of frequency of absorption (cm$^{-1}$). Concentrations were carried out at reduced pressure using a rotary evaporator.

In one embodiment, halo-isatin derivatives were prepared according to the conventional organic synthesis methods, or were obtained from commercial source. As used herein, halo-isatin derivatives are isatin derivatives having a structure of Structure I, wherein Y is C, $R_1$, $R_2$, $R_3$ and $R_4$ are H or halogen; $R_5$ is H, and $R_6$, and $R_7$ are taken together as =O.

The isatin derivatives comprising the structure of Structure I can be prepared following one or more synthesis procedure(s) described below.

Example 1a: Substitution at 1-N-Position of Isatin Derivatives (i.e. Isatin Derivatives Wherein $R_5$ were not H)

In another embodiment, isatin derivatives comprising a structure of Structure I, wherein $R_5$ is not H were prepared by N-alkylation reduction of the corresponding isatin derivatives wherein $R_5$ is H. Scheme 1 showed an exemplary preparation using an isatin derivative comprising a structure of Structure I as an example.

Scheme 1. Preparation of isatin derivatives by N-alkylation reduction

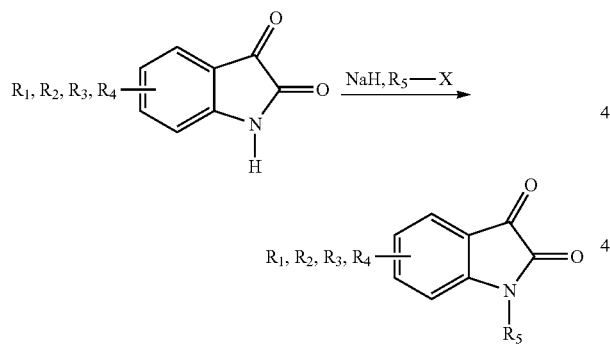

$R_1$, $R_2$, $R_3$, $R_4$, $R_5$ and $R_6$ are defined as supra, and X is F, Cl, Br, or I; preferably X is Br, Cl, or I.

For example, Compound 3 (N-benzyl-6-bromoindoline-2,3-dione) was prepared according to Scheme 1a:

Scheme 1a. Synthesis of Compound 3 by N-alkylation Reduction

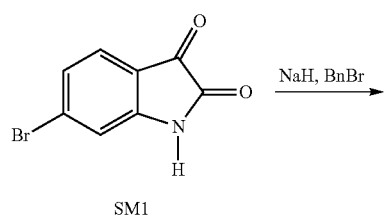

SM1

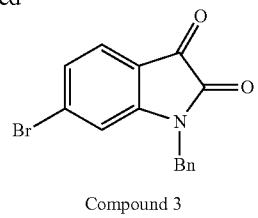

Compound 3

6-Bromoisatin (SM1) (984 mg, 4.35 mmol, 1.0 equiv) was dissolved in N,N-dimethylformamide (8.70 mL), and the orange solution was cooled to 0° C. Sodium hydride (183 mg, 4.57 mmol, 60% dispersion in mineral oil, 1.05 equiv) was added in two portions, and the resulting purple suspension was maintained at 0° C. for 15 min. Benzyl bromide (604 μL, 5.05 mmol, 1.16 mmol) was added dropwise, and the resultant orange solution was maintained at 0° C. for 30 min. Water (30 mL) was added, and the biphasic mixture was extracted with EtOAc (4×50 mL). The combined organics were dried over Na$_2$SO$_4$ and concentrated. Purification of the residue by silica gel flash column chromatography (gradient 1:3 EtOAc-hexanes to 100% EtOAc) gave Compound 3 (1.31 g, 95%) as an orange solid: mp 190~192° C.; $R_f$ 0.69 (3:7 EtOAc-hexanes); 1H NMR (500 MHz, CDCl$_3$): δ 7.47 (d, J=7.9 Hz, 1H), 7.41~7.36 (m, 2H), 7.36~7.31 (m, 3H), 7.28~7.24 (m, 1H), 6.96 (d, J=1.4, 1H), 4.91 (s, 2H); $^{13}$C NMR (125 MHz, CDCl$_3$): δ 182.1 (C), 158.3 (C), 151.6 (C), 134.2 (C), 133.7 (C), 129.4 (CH), 128.6 (CH), 127.6 (CH), 127.3 (CH), 126.5 (CH), 116.5 (C), 114.7 (CH), 44.4 (CH$_2$); IR (film): 1733, 1603 cm~1; HRMS-ESI (m/z) [M+Na]$^+$ calcd. for C$_{15}$H$_{10}$NO$_2$BrNa, 337.9792, found, 337.9786.

In another example, Compound 4 (N-benzyl-5-iodoindoline-2,3-dione) was prepared according to Scheme 1b:

Scheme 1b. Synthesis of Compound 4 by N-alkylation Reduction

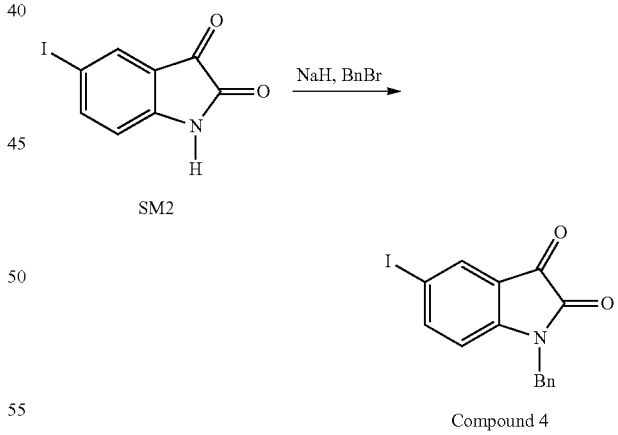

5-Iodoisatin (SM2) (871 mg, 3.19 mmol, 1.0 equiv) was dissolved in N,N-dimethylformamide (6.40 mL), and the red solution was cooled to 0° C. Sodium hydride (134 mg, 3.35 mmol, 60% dispersion in mineral oil, 1.05 equiv) was added in two portions, and the resulting purple suspension was maintained at 0° C. for 15 min. Benzyl bromide (443 μL, 3.70 mmol, 1.16 mmol) was added dropwise, and the resultant red solution was maintained at 0° C. for 30 min. Water (20 mL) was added, and the biphasic mixture was extracted with EtOAc (4×50 mL). The combined organics were dried over $Na_2SO_4$ and concentrated under reduced pressure. Purification via silica gel flash column chromatography (3:7 EtOAc-hexanes) gave Compound 4 (1.29 g, 88%) as a red solid with melting point and $^1$H NMR data consistent with previously reported: 15 mp 150~152° C.; $R_f$ 0.32 (1:3 EtOAc-hexanes); $^1$H NMR (500 MHz, $CDCl_3$): δ 7.86 (d, J=1.6, 1H), 7.76 (dd, J=8.3, 1.7, 1H), 7.37~7.28 (m, 5H), 6.59 (d, J=8.3, 1H), 4.92 (s, 2H); $^{13}$C NMR (125 MHz, $CDCl_3$): δ 182.0 (C), 157.4 (C), 150.1 (C), 146.5 (CH), 134.2 (C), 133.9 (CH), 129.3 (CH), 128.5 (CH), 127.5 (CH), 119.3 (C), 113.3 (CH), 86.4 (C), 44.2 ($CH_2$); IR (film): 1733, 1603 $cm^{-1}$; HRMS-ESI (m/z) $[M+Na]^+$ calcd for $C_{15}H_{10}INO_2Na$, 385.9654, found, 385.9659.

In another example, N-benzylindoline-2,3-dione (S1) is prepared according to Scheme 1c:

Scheme 1c. Preparation of N-benzylindoline-2,3-dione (S1)

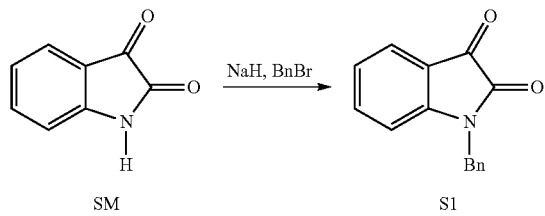

Isatin (SM) (10.0 g, 68.0 mmol, 1.0 equiv) was dissolved in N,N-dimethylformamide (125 mL), and the resultant solution was cooled to 0° C. Sodium hydride (2.85 g, 71.4 mmol, 60% dispersion in mineral oil, 1.05 equiv) was added in three portions resulting in a purple suspension. The mixture was maintained at 0° C. for 15 min. Benzyl bromide (9.43 mL, 78.8 mmol, 1.16 equiv) was added dropwise, and the brown solution was maintained at 0° C. for 15 min. Ice-cooled water (600 mL) was added to the mixture, and a precipitate formed. The precipitate was filtered, washed with water (60 mL) and hexanes (30 mL). This solid was recrystallized from hot ethanol (240 mL), filtered and dried under reduced pressure to afford compound S1 (15.1 g, 94%) as red-needlelike crystals. Melting point and $^1$H NMR data were consistent with previously reported values:[59-60] mp 131~132° C.; $R_f$ 0.61 (2:3 EtOAc:hexane) $^1$H NMR (500 MHz, $CDCl_3$): δ 7.54 (d, J=7.4, 1H), 7.45 (t, J=7.8, 1H), 7.33~7.24 (m, 5H), 7.04 (t, J=7.5, 1H), 6.77 (d, J=8.0, 1H), 4.89 (s, 2H); $^{13}$C NMR (125 MHz, $CDCl_3$): δ 183.3 (C), 158.3 (C), 150.7 (C), 138.5 (CH), 134.6 (C), 129.1 (CH), 128.2 (CH), 127.5 (CH), 125.3 (CH), 123.9 (CH), 117.7 (C), 111.1 (CH), 44.0 ($CH_2$); IR (film): 1729, 1609, $cm^{-1}$; HRMS-ESI (m/z) $[M+Na]^+$ calcd for $C_{15}H_{11}NO_2Na$, 260.0688, found, 260.0692.

In another example, N-((2-(trimethylsilyl)ethoxy)methyl) indoline-2,3-dione (S2) is prepared according to Scheme 1d:

Scheme 1d. Preparation of N-((2-(trimethylsilyl)ethoxy)methyl)indoline-2,3-dione (S2)

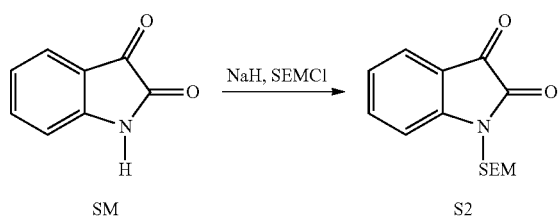

To a rapidly stirring suspension of isatin (SM) (22.0 g, 150 mmol, 1.0 equiv) and N,N-dimethylformamide (237 mL) was added sodium hydride (7.18 g, 179.4 mmol, 60% dispersion in mineral oil, 1.2 equiv) at rt. The suspension was stirred for 20 min, cooled to 0° C., and 2-(trimethylsilyl)ethoxymethyl chloride (32.3 mL, 178 mmol, 1.19 equiv) was added dropwise. The solution was then allowed to warm to rt. After 2 hr, the reaction mixture was quenched by pouring into brine (200 mL) and the resulting mixture was cooled to 0° C. The aqueous layer was separated and extracted with EtOAc (4×200 mL). The combined organic layers were washed with saturated aqueous lithium chloride (400 mL), then dried over $MgSO_4$ and concentrated to yield a brown solid. This solid was further purified by silica gel flash column chromatography (gradient: 1:8 $Et_2O$-hexanes to 1:2 $Et_2O$-hexanes) to afford isatin S2[61] (30.4 g, 74%) as an orange solid: mp 61~62° C.; $R_f$ 0.57 (1:1 EtOAc-hexanes); $^1$H NMR (500 MHz. $CDCl_3$) δ 7.65 (t, J=7.6, 1H), 7.63 (td, J=7.6, 1.4, 1H), 7.18 (td, J=7.6, 0.8, 1H), 7.14 (t, J=8.1, 1H), 5.17 (s, 2H), 3.60 (d, J=8.3, 2H), 0.94 (d, J=8.3, 2H), ~0.02 (s, 9H); $^{13}$C NMR (125 MHz, $CDCl_3$) δ 183.1 (C), 158.3 (C), 150.4 (C), 138.7 (CH), 125.4 (CH), 124.3 (CH), 117.5 (C), 111.7 (CH), 69.8 ($CH_2$), 66.8 ($CH_2$), 17.9 ($CH_2$), ~1.4 ($CH_3$); IR (film) 2954, 1742, 1611 $cm^{-1}$; HRMS-ESI (m/z) $[M+Na]^+$ calcd for $C_{14}H_{19}NO_3SiNa$, 300.1032, found, 300.1038.

In another example, 7-fluoro-N-((2-(trimethylsilyl) ethoxy)methyl)indoline-2,3-dione (S3) is prepared according to Scheme 1e:

Scheme 1e. Preparation of 7-fluoro-N-((2-(trimethylsilyl)ethoxy)methyl)indoline-2,3-dione (S3)

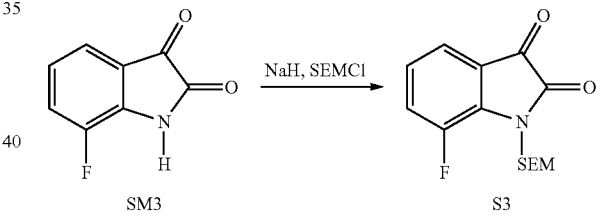

7-Fluoroisatin (SM3) (1.50 g, 9.08 mmol, 1.0 equiv) was dissolved in N,N-dimethylformamide (30 mL), and the resultant red solution was cooled to 0° C. Sodium hydride (436 mg, 10.9 mmol, 60% dispersion in mineral oil, 1.2 equiv) was added in two portions resulting in a purple suspension. The mixture was allowed to warm to rt for 20 min with vigorous stirring, then cooled to 0° C. 2-(Trimethylsilyl)ethoxymethyl chloride (1.91 mL, 10.8 mmol, 1.2 equiv) was added dropwise, and the dark brown solution was maintained at 0° C. for 1.5 hr, then poured into brine (10 mL) at 0° C. The resulting mixture was extracted with $Et_2O$ (4×20 mL), and the combined organic extracts were dried over $Na_2SO_4$, and concentrated. Purification of the residue by silica gel flash column chromatography (1:4 EtOAc-hexanes) gave isatin derivative S3 (2.44 g, 91%) as an orange solid: mp 55~56° C.; $R_f$ 0.51 (1:3 EtOAc-hexanes); $^1$H NMR (500 MHz, $CDCl_3$): δ 7.40 (d, J=7.5, 1H), 7.34 (dd J=11.1, 8.4, 1H), 7.09 (td, J=11.6, 3.9, 1H), 5.19 (s, 2H), 3.56 (t, J=7.7, 2H), 0.87 (t, J=7.7, 2H), ~0.10 (s, 9H); $^{13}$C NMR (125 MHz, $CDCl_3$): δ 182.8 (d, J=1.9, C), 158.1 (C), 148.5 (d, J=249.2, C), 136.5 (d, J=9.6, C), 126.6 (d, J=19.6, CH), 125.2 (d, J=5.8, CH), 121.4 (d, J=3.4, CH), 120.6, (d, J=2.5, C), 71.2, (d, J=4.9, $CH_2$), 66.9 ($CH_2$), 17.8 ($CH_2$), ~1.5 (CH$_3$); IR (film): 1746, 1627 cm$^{-1}$; HRMS-ESI (m/z) [M+Na]$^+$ calcd for C$_{14}$H$_{18}$FNO$_3$SiNa, 318.0938, found, 318.0935.

In another example, 4-iodo-N-methyl-indoline-2,3-dione (S4) is prepared according to Scheme 1f:

Scheme 1f. Preparation of 4-iodo-N-methyl-indoline-2,3-dione (S4)

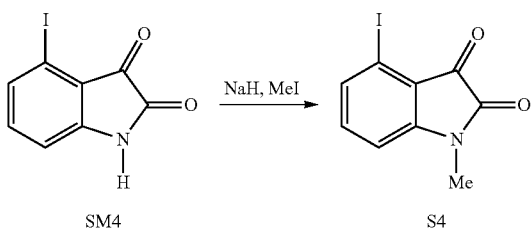

To a solution of 4-iodoisatin (SM4) (11.7 g, 42.8 mmol, 1.0 equiv) and N,N-dimethylformamide (70 mL) at rt was added sodium hydride (2.57 g, 64.2 mmol, 60% dispersion in mineral oil, 1.5 equiv) resulting in an exotherm and a dark purple solution. After 5 min, methyl iodide (3.20 mL, 51.4 mmol, filtered through basic alumina, 1.2 equiv) was added rapidly using a syringe. The resulting dark brown solution was maintained at rt for 20 min and then poured into brine at 0° C. The resulting mixture was allowed to stand at 0° C. for 2 hr forming a dark brown precipitate. This precipitate was collected by vacuum filtration, and was washed with H$_2$O (300 mL) and hexanes (200 mL) to provide 12.3 g (100%) of isatin derivative S4. $^1$H NMR (400 MHz, d$_6$-DMSO) δ 7.55 (d, J=7.9, 1H), 7.36 (t, J=7.9, 1H), 7.16 (d, J=7.8, 1H), 3.15 (s, 3H); $^{13}$C NMR (100 MHz, CDCl$_3$) 182.0, 158.0, 153.4, 133.7, 118.0, 110.2, 92.8, 25.8; IR (film) 1731, 1592 cm$^{-1}$; HRMS-ESI calcd for C$_9$H$_6$INO$_2$ (M$^+$) 286.9443, found 286.9447.

In another example, N-methyl-7-methoxyindoline-2,3-dione (S5) is prepared according to Scheme 1h:

Scheme 1h. Preparation of N-methyl-7-methoxyindoline-2,3-dione (S5).

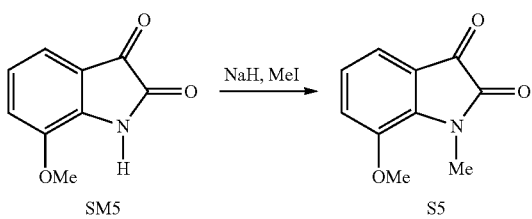

To a solution of 7-methoxyindoline-2,3-dione (SM5) (16.7 g, 94.3 mmol, 1.0 equiv) and N,N-dimethylformamide (205 mL) was added sodium hydride (4.41 g, 104 mmol, 60% dispersion in mineral oil, 1.1 equiv) at rt. After 10 min, iodomethane (6.45 mL, 104 mmol, 1.1 equiv) was added, and the reaction mixture was maintained at rt for 4 hr. The reaction mixture was then poured into ice water (800 mL) and the resulting dark red precipitate was collected by vacuum filtration. The solid was washed with water (2×300 mL), redissolved in dichloromethane (700 mL), dried over MgSO$_4$, and concentrated to provide isatin S5 (16.1 g, 90%) as a dark red solid: $^1$H NMR (500 MHz, CDCl$_3$) δ 7.22 (dd, J=7.4, 1.1, 1H), 7.16 (dd, J=8.3, 1.0, 1H), 7.04 (dd, J=8.3, 7.4, 1H), 3.90 (s, 3H), 3.50 (s, 3H), 0.95 (s, 3H); HRMS-ESI (m/z) [M+Na]$^+$ calcd for C$_{10}$H$_9$NO$_3$Na, 214.0480, found, 214.0482.

Example 1b: Substitution at 4, 5, 6, and/or 7 Position(s) of Isatin Derivatives (i.e. R$_1$, R$_2$, R$_3$, and/or R$_4$ were/was not H)

In another embodiment, isatin derivatives comprising a structure of Structure I as disclosed herein were prepared by Suzuki-Miyaura coupling of N-protected haloisatins and the corresponding organotrifluoroborates. Scheme 2 showed an exemplary preparation using substitution with R$_1$ of an isatin derivative comprising a structure of Structure I as an example, wherein X is halogen, e.g. F, Cl, Br or I. The same synthesis strategy can be applied on substitution(s) of R$_2$, R$_3$ and/or R$_4$ of an isatin derivative comprising a structure of Structure I.

Scheme 2. Preparation of isatin derivatives by Suzuki-Miyaura coupling.

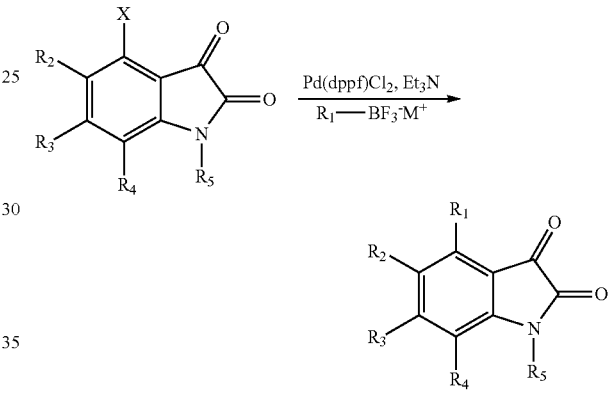

In one example, Compound 1 was prepared according to Scheme 2a:

Scheme 2a. Preparation of Compound 1.

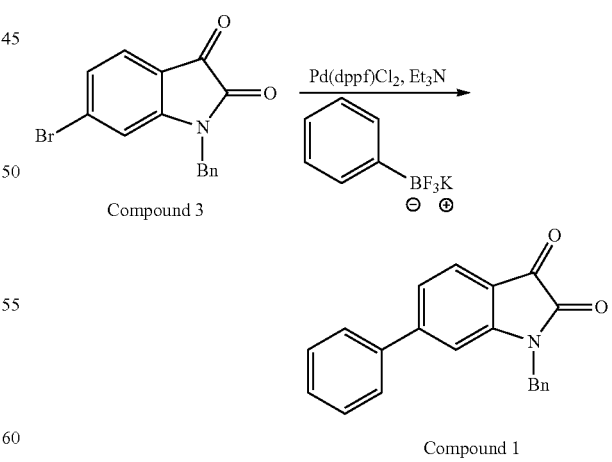

Compound 3 (984 mg, 4.35 mmol, 1.0 equiv) was dissolved in N,N-dimethylformamide (8.70 mL), and the orange solution was cooled to 0° C. Sodium hydride (183 mg, 4.57 mmol, 60% dispersion in mineral oil, 1.05 equiv) was added in two portions, and the resulting purple suspension was maintained at 0° C. for 15 min. Benzyl bromide (604 μL, 5.05 mmol, 1.16 mmol) was added dropwise, and the resultant orange solution was maintained at 0° C. for 30 min. Water (30 mL) was added, and the biphasic mixture was extracted with EtOAc (4×50 mL). The combined organics were dried over $Na_2SO_4$ and concentrated. Purification of the residue by silica gel flash column chromatography (gradient 1:3 EtOAc-hexanes to 100% EtOAc) gave Compound 1 (1.31 g, 95%) as an orange solid: mp 190~192° C.; $R_f$ 0.69 (3:7 EtOAc-hexanes); $^1$H NMR (500 MHz, $CDCl_3$): δ 7.47 (d, J=7.9 Hz, 1H), 7.41~7.36 (m, 2H), 7.36~7.31 (m, 3H), 7.28~7.24 (m, 1H), 6.96 (d, J=1.4, 1H), 4.91 (s, 2H); $^{13}$C NMR (125 MHz, CDCl3): δ 182.1 (C), 158.3 (C), 151.6 (C), 134.2 (C), 133.7 (C), 129.4 (CH), 128.6 (CH), 127.6 (CH), 127.3 (CH), 126.5 (CH), 116.5 (C), 114.7 (CH), 44.4 ($CH_2$); IR (film): 1733, 1603 $cm^{-1}$; HRMS-ESI (m/z) $[M+Na]^+$ calcd for $C_{15}H_{10}NO_2BrNa$, 337.9792, found, 337.9786.

In another embodiment, Compound 2 was prepared according to Scheme 2b:

Scheme 2b. Preparation of Compound 2.

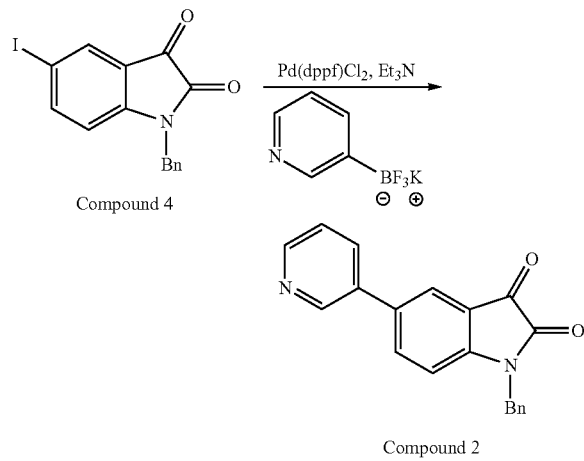

Prior to use, all liquids (isopropanol, water, and triethylamine) were degassed by bubbling argon through stock solutions for 30 min. Compound 4 (910 mg, 2.51 mmol, 1.0 equiv) was suspended in isopropanol (16 mL) and water (8 mL). Potassium 3-pyridyltrifluoroborate (510 mg, 2.76 mmol, 1.1 equiv) and dichloro[1,1'-bis(diphenylphosphino)ferrocene]palladium (II) dichloromethane complex (47 mg, 50.1 μmol, 0.02 equiv) were added, followed by triethylamine (1.05 mL, 7.52 mmol, 3.0 equiv). The red suspension was heated to reflux (oil bath at 98° C.) for 2 hr, resulting in a brown solution. After allowing this solution to cool to rt, water (20 mL) was added, and the mixture was extracted with EtOAc (4×50 mL). The combined organic extracts were dried over $Na_2SO_4$ and concentrated. Purification of the residue by silica gel flash column chromatography (gradient 1:1 EtOAc-hexanes to 100% EtOAc) gave Compound 2 (570 mg, 72%) as an orange-red solid: mp 168~169° C.; $R_f$ 0.43 (100% EtOAc); $^1$H NMR (500 MHz, $CDCl_3$): δ 8.77 (s, 1H), 8.62 (d, J=4.1, 1H), 7.84 (s, 1H), 7.79 (d, J=7.9, 1H), 7.71 (d, J=8.2, 1H), 7.40~7.33 (m, 6H), 6.91 (d, J=8.2, 1H), 4.99 (s, 2H); $^{13}$C NMR (125 MHz, $CDCl_3$): δ 183.2 (C), 158.4 (C), 150.6 (C), 149.3 (CH), 147.9 (CH), 136.9 (CH), 134.8 (C), 134.5 (C), 134.2 (C), 134.0 (CH), 129.4 (CH), 128.5 (CH), 127.7 (CH), 124.1 (CH), 123.9 (CH), 118.5 (C), 111.9 (CH), 44.5 ($CH_2$); IR (film): 1737, 1619 $cm^{-1}$; HRMS-ESI (m/z) $[M+H]^+$ calcd for $C_{20}H_{15}N_2O_2$, 315.1133, found, 315.1129.

In another example, compound S6 was prepared according to Scheme 2c:

Scheme 2c. Preparation of S6

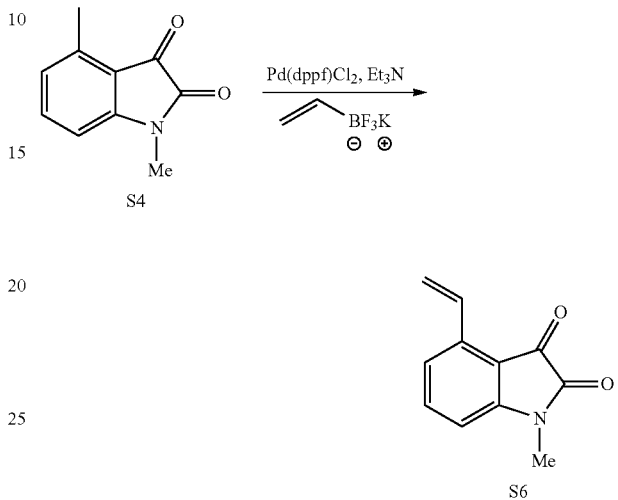

The general procedure of Molander was followed.[62] Prior to carrying out this reaction all liquids (isopropanol, water and triethylamine) were degassed by bubbling argon thought stock solutions for 30 min. To a suspension of S4 (1.86 g, 6.48 mmol, 1.0 equiv), potassium vinyltrifluoroborate (955 mg g, 7.12 mmol, 1.1 equiv), [1,1'-bis(diphenylphosphino)ferrocene]palladium (II)] dichloromethane complex (95 mg, 0.13 mmol, 0.02 equiv), and i-PrOH:$H_2O$ (2:1, 43.5:21.25 mL) was added triethylamine (2.71, 19.4 mmol, 3.0 equiv). The resulting suspension was heated to reflux (oil bath at 98° C.) for 2 hr. After this time, the reaction mixture was diluted with water (60 mL) and EtOAc (60 mL). The aqueous layer was separated and extracted with EtOAc (4×75 mL). The combined organic layers were washed with 1 M aqueous $NaHSO_4$ (250 mL) then dried over $MgSO_4$ and concentrated to yield a red solid. This solid was further purified by silica gel flash column chromatography (100% $CH_2Cl_2$) to afford S6 (913 mg, 75%) as a red solid: mp 129~132° C.; $R_f$ 0.61 (1:5 ($Et_2O$—$CH_2Cl_2$); $^1$H NMR (500 MHz. CDCl3) δ 7.59 (dd, J=17.6, 11.0, 1H), 7.50 (t, J=8.0, 1H), 7.37 (d, J=8.0, 1H), 6.75 (d, J=8.0, 1H), 6.03 (t, J=7.7, 1H), 5.58 (d, J=17.6 Hz, 1H), 3.24 (s, 3H); $^{13}$C NMR (125 MHz, $CDCl_3$) δ 183.6 (C), 158.0 (C), 151.3 (C), 138.6 (C), 137.6 (CH), 131.0 (CH), 120.7 ($CH_2$), 119.9 (CH), 113.6 (C), 108.5 (CH), 26.3 ($CH_3$); IR (film) 1733, 1578 $cm^{-1}$; HRMS (ES) (m/z) $[M+Na]^+$ calcd for $C_{11}H_9NO_2Na$, 219.0531, found, 210.0527.

Example 1c: Preparation of Isatin Derivatives Having 2H on Position 3

In another embodiment, isatin derivatives having an oxo group on position 3 were prepared by reduction reaction of the corresponding isatin derivatives. Scheme 3 showed an exemplary preparation using an isatin derivative comprising a structure of Structure I as an example.

Scheme 3. Preparation of isatin derivatives by 3-reduction reaction

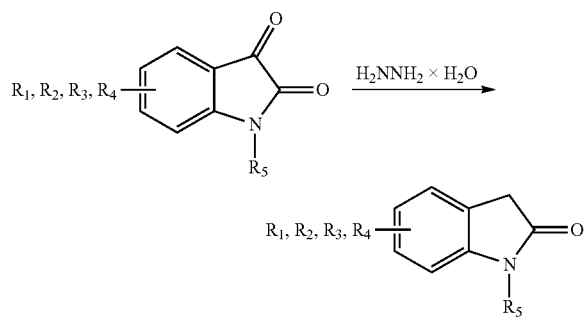

In one example, N-benzylindolin-2-one (S7) was prepared according to Scheme 3a:

Scheme 3a. Preparation of N-benzylindolin-2-one (S7)

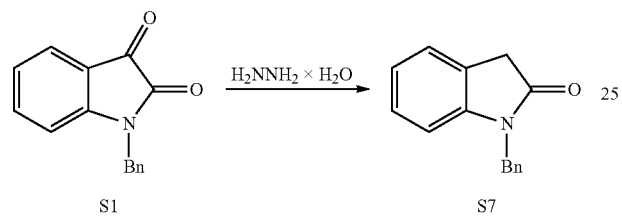

A suspension of S1 (1.51 g, 6.36 mmol, 1.0 equiv) and hydrazine.hydrate (12.0 mL, 191 mol, 51% solution, 30.0 equiv) was heated to 130° C. for 3 hr. After this time, the reaction mixture was allowed to cool to rt and was partitioned between brine (20 mL) and EtOAc (30 mL). The aqueous layer was separated and extracted with EtOAc (3×20 mL). The combined organic layers were washed with saturated aqueous NaHCO$_3$ (20 mL), then dried over Na$_2$SO$_4$ and concentrated to yield a yellow oil. This oil was further purified by silica gel flash column chromatography (1:4 EtOAc-hexanes) to afford oxindole S7, (1.31 g, 92%) as a yellow oil. $^1$H NMR data was consistent with previously reported values:[59-60] R$_f$ 0.61 (2:3 EtOAc-hexanes); $^1$H NMR (500 MHz. CDCl$_3$) δ 7.33~7.26 (m, 4H), 7.22 (m, 2H), 7.14 (t, J=7.7, 1H), 6.97 (t, J=7.5, 1H), 6.71 (d, J=7.8, 1H), 4.88 (s, 2H), 3.55 (s, 2H); $^{13}$C NMR (125 MHz, CDCl$_3$) δ 174.9 (C), 144.2 (C), 135.9 (C), 128.6 (CH), 127.7 (CH), 127.5 (CH), 127.3 (CH), 124.4 (C), 124.3 (CH), 122.2 (CH), 108.9 (CH), 43.5 (CH$_2$), 35.6 (CH$_2$); IR (film) 1702, 1613 cm$^{-1}$; HRMS-ESI (m/z) [M+Na]$^+$ calcd for C$_{15}$H$_{13}$NONa, 246.0895, found, 246.0896.

In one example, N-((2-(trimethylsilyl)ethoxy)methyl)indolin-2-one (S8) was prepared according to Scheme 3b:

Scheme 3b. Preparation of N-((2-(trimethylsilyl)ethoxy)methyl)indolin-2-one (S8)

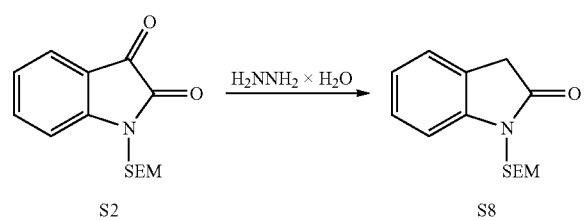

A suspension of S2 (5.78 g, 20.8 mmol, 1.0 equiv) and hydrazine.hydrate (40.0 mL, 625 mol, 51% solution, 30.0 equiv) was heated to 130° C. for 3 hr. After this time, the reaction mixture was allowed to cool to rt and partitioned between brine (30 mL) and EtOAc (40 mL). The aqueous layer was separated and extracted with EtOAc (4×40 mL). The combined organic layers were washed with 1 M aqueous NaHSO$_4$ (200 mL), dried over MgSO$_4$, and concentrated under reduced pressure to yield a yellow oil. This oil was further purified by silica gel flash column chromatography (gradient: 1:5 Et$_2$O-hexanes to 1:4 Et$_2$O-hexanes) to afford S8, (4.95 g, 90%) as a yellow oil showing NMR data consistent to previously reported values:[63] R$_f$ 0.44 (1:4 EtOAc-hexanes); $^1$H NMR (500 MHz. CDCl$_3$) δ 7.31~7.24 (m, 2H), 7.05 (d, J=7.6, 1H), 7.02, (d, J=8.1, 1H), 5.13 (s, 2H), 3.58~3.55 (m, 4H), 0.94 (d, J=8.3, 2H), ~0.05 (s, 9H); $^{13}$C NMR (125 MHz, CDCl$_3$) δ 175.5 (C), 143.7 (C), 128.0 (CH), 124.4 (CH), 124.0 (C), 122.8 (CH), 109.7 (CH), 69.5 (CH$_2$), 66.2 (CH$_2$), 36.0 (CH$_2$), 17.9 (CH$_2$), ~1.4 (CH$_3$); IR (film) 2954, 1725, 1615, cm$^{-1}$; HRMS-ESI (m/z) [M+Na]$^+$ calcd for C$_{14}$H$_{21}$NO$_2$SiNa, 286.1239, found, 286.1238.

In one example, N-methyl-7-methoxyindolin-2-one (S9) was prepared according to Scheme 3c:

Scheme 3c. Preparation of N-methyl-7-methoxyindolin-2-one (S9)

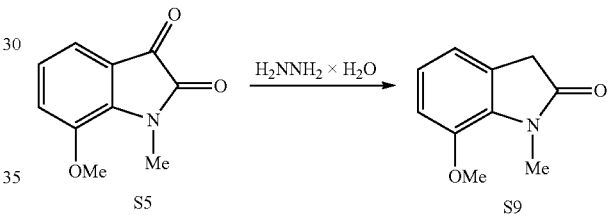

A suspension of S5 (16.1 g, 83.9 mmol, 1.0 equiv) and hydrazine.hydrate (160 mL, 2.52 mol, 51% solution, 30.0 equiv) was heated to 130° C. for 3 hr. After this time, the reaction mixture was allowed to cool to rt and then was partitioned between brine (160 mL) and ethyl acetate (200 mL). The aqueous layer was separated and extracted with ethyl acetate (3×100 mL). The combined organic layers were washed with 1 M aqueous NaHSO$_4$ (2×300 mL), dried over MgSO$_4$ and concentrated to afford S9 (14.8 g, 99%) as a beige solid showing $^1$H NMR and melting point data consistent with previously reported values:[64] mp 95~97° C.; R$_f$ 0.50 (1:1 EtOAc-hexanes); $^1$H NMR (500 MHz, CDCl3) δ 6.96 (dd, J=8.0, 8.0 1H), 6.84 (m, 2H), 3.84 (s, 3H), 3.48 (s, 2H), 3.47 (s, 3H); $^{13}$C NMR (125 MHz, CDCl$_3$) δ 175.4, 145.4, 133.2, 126.1, 122.9 (CH), 117.3 (CH), 111.9 (CH), 56.1 (CH$_3$), 36.2 (CH$_2$), 29.6 (CH$_3$); IR (film) 2948, 1706, 1615 cm$^{-1}$; HRMS-ESI (m/z) [M+Na]$^+$ calcd for C$_{10}$H$_{11}$NO$_2$Na, 200.0687, found, 200.0690.

Example 1d: Preparation of Isatin Derivatives Comprising a Structure of Structure I, Wherein R6 and R7 Taken Together is =N—OR"

In another embodiment, an isatin derivative comprising a structure of Structure I, wherein R6 and R7 taken together is =N—OR", was prepared by a conventional Schiff base preparation (Scheme 4):

Scheme 4. Preparation of an isatin derivative comprising by Schift base preparation

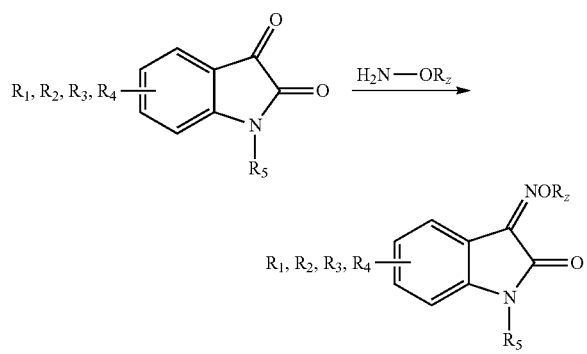

Example 1e: Preparation of Compound 12 (N-(2-Thienylmethyl)-5-(pyridin-3-yl)indoline-2,3-dione)

Following the procedure described for the preparation of Compound 4, 5-iodoisatin (20 mg, 0.073 mmol) was alkylated with 2-(bromomethyl)thiophene (17 mg, 0.096 mmol). The resulting crude N-alkylation product (16 mg) was coupled with potassium 3-pyridyltrifluoroborate (9 mg, 0.048 mmol) following the procedure described for the preparation of Compound 2. The crude residue was purified on silica gel (50~70% EtOAc-hexanes) to give 4.4. mg (19%) of Compound 12: $^1$H NMR (500 MHz, CDCl$_3$): δ 8.80 (br s, 1H), 8.63 (br s, 1H), 7.84 (s, 1H), 7.82 (br d, J=6.6, 1H), 7.78 (dd, J=7.1, 1.6, 1H), 7.39 (dd, J=6.5, 3.9, 1H), 7.28 (br s, 1H), 7.15 (d, J=2.5 Hz, 1H), 7.10 (d, J=6.8 Hz, 1H), 7.00 (m, 1H), 5.15 (s, 2H); HRMS-ESI (m/z) [M+H]$^+$ calcd for C$_{18}$H$_{13}$N$_2$O$_2$S, 321.0698, found, 312.0856.

Example 1f: Preparation of Compound 13 (N-Benzyl-3-hydroxy-5-(pyridin-3-yl)indoline-2-one)

Sodium borohydride (1.2 mg, 0.32 mmol) was added to a solution of N-benzyl-5-(pyridin-3-yl)indoline-2,3-dione (10 mg, 0.032 mmol), THF (0.3 mL) and THF (0.3 mL) cooled to 0° C. After 10 min, the reaction was quenched with acetic acid, diluted with EtOAc, and washed with aq NaHCO$_3$. After drying (MgSO$_4$), the solvent was evaporated and the residue was purified by chromatography on silica gel (3:1 EtOAc-hexanes) to give 10 mg (98%) of Compound 13: $^1$H NMR (500 MHz, CDCl$_3$): δ 8.71 (br s, 1H), 8.56 (br s, 1H), 7.81 (d, J=7.8, 1H), 7.68 (s, 1H), 7.40 (d, J=8.5, 1H), 7.40~7.30 (m, 6H), 6.80 (d, J=8.0, 1H), 5.26 (s, 1H), 4.96 (d, J=8.0, 1H), 4.89 (d, J=8.0, 1H), 4.6~4.9 (m, 1H); MS-ESI (m/z) [M+H]$^+$ calcd for C$_{20}$H$_{17}$N$_2$O$_2$, 317.13; found 317.19.

Example 1g: Preparation of Compound 14 (3-Acetoxy-N-Benzyl-5-(pyridin-3-yl)indoline-2-one)

N-Benzyl-3-hydroxy-5-(pyridin-3-yl)indoline-2-one (12 mg, 0.038 mmol) was acetylated in CH$_2$Cl$_2$ (0.2 mL) in standard fashion with Ac$_2$O (8 μL) and DMAP (2 mg). Purification of the crude product on silica gel (50~60% EtOAc-hexanes) gave 10 mg (73%) of Compound 14: $^1$H NMR (500 MHz, CDCl$_3$): δ 8.75 (br s, 1H), 8.57 (br s, 1H), 7.79 (d, J=7.6, 1H), 7.58 (s, 1H), 7.45 (d, J=8.1, 1H), 7.40~7.25 (m, 6H), 6.81 (d, J=8.0, 1H), 6.08 (s, 1H), 4.99 (d, J=15.0, 1H), 4.93 (d, J=15, 1H), 2.25 (s, 3H); MS-ESI (m/z) [M+H]$^+$ calcd for C$_{22}$H$_{19}$N$_2$O$_2$, 359.14; found 359.20.

Example 1h: Preparation of Compound 15 (N-Benzyl-5-(pyridin-3-yl)indoline-2-one)

A mixture of Compound 2 (10 mg, 0.032 mmol) and hydrazine hydrate was stirred in a vial at 140° C. for 4 hr. After cooling to room temperature, the reaction was diluted with 200 μL of water and the pH was adjusted to ~2. The reaction was diluted with sat. aq. NaHCO$_3$, and extracted with CH$_2$Cl$_2$. After drying (MgSO$_4$), the solvent was evaporated and the residue was purified by chromatography on silica gel (40~50% EtOAc-hexanes) to give 3.2 mg (34%) of Compound 15: $^1$H NMR (500 MHz, CDCl$_3$): δ 8.78 (br s, 1H), 8.56 (br d, J=3.9 Hz, 1H), 7.79 (br d, J=5.1, 1H), 7.49 (s, 1H), 7.39 (d, J=6.8, 1H), 7.25~7.35 (m, 6H), 6.83 (d, J=6.8, 1H), 4.97 (s, 2H), 3.71 (s, 2H); MS-ESI (m/z) [M+H]$^+$ calcd for C$_{20}$H$_{17}$N$_2$O, 301.13; found 301.2.

Example 1i: Preparation of Compound 16 (N-(3-Thienylmethyl)-5-(pyridin-3-yl)indoline-2,3-dione)

Following the procedure described for the preparation of Compound 4, 5-iodoisatin (25 mg, 0.092 mmol) was alkylated with 3-(bromomethyl)thiophene (24 mg, 0.14 mmol) to give 22 mg of the N-alkylation product. A 15 mg sample of this product was coupled with potassium 3-pyridyltrifluoroborate (9 mg, 0.048 mmol) following the procedure described for the preparation of Compound 2. The crude product was purified on silica gel (50~70% EtOAc-hexanes) to give 11 mg (54%) of Compound 16: $^1$H NMR (500 MHz, CDCl$_3$): δ 8.78 (br s, 1H), 8.62 (br s, 1H), 7.84 (s, 1H), 7.81 (br d, J=8.0, 1H), 7.76 (d, J=6.8, 1H), 7.39 (dd, J=6.6, 4.0 Hz, 1H), 7.35 (br s, 1H), 7.30 (s, 1H), 7.09 (br d, J=4.1 Hz, 1H), 7.00 (d, J=6.8 Hz, 1H), 4.99 (s, 2H); HRMS-ESI (m/z) [M+H]$^+$ calcd for C$_{18}$H$_{13}$N$_2$O$_2$S, 321.0658, found, 321.0751.

Example 1j: Preparation of Compound 17 (N-Benzyl-5-(pyridin-3-yl)-1H-pyrrolo[2,3-b]pyridine-2,3-dione)

Following the procedure described for the preparation of Compound 2, N-benzyl-5-bromo-1,3-dihydro-2H-pyrrolo[2,3-b]pyridine-2-one (48 mg, 0.15 mmol, T. Jiro; T. Zhiwei; Y. Tsuchiya; T. Ito ARKIVOC 2009, 2, 132) was coupled with potassium 3-pyridyltrifluoroborate (30 mg, 0.16 mmol). The crude product was purified on silica gel (50~70% EtOAc-hexanes) to give 33 mg (73%) of N-benzyl-5-(pyridin-3-yl)-1,3-dihydro-2H-pyrrolo[2,3-b]pyridine-2-one. A 12 mg sample of this product was dissolved in aqueous acetic acid (30% H$_2$O, 0.6 mL), 5 mg of SeO$_2$ was added and the mixture was heated at 60° C. for 16 hr. After concentration, the residue was partitioned between sat. aq. NaHCO$_3$ and CH$_2$Cl$_2$, the organic phase was dried (MgSO$_4$), concentrated and the residue purified on silica gel (1~2% MeOH—CHCl$_3$) to give 3.8 mg (22%) of Compound 17: $^1$H NMR (500 MHz, CDCl$_3$): δ 9.84 (s, 1H), 8.93 (s, 1H), 8.67 (s 1H), 8.52 (br s, 1H), 8.01 (br s, 1H), 7.60~7.25 (m, 7H), 5.16 (s, 2H); MS-ESI (m/z) [M+H+ MeOH]$^+$ calcd for C$_{20}$H$_{18}$N$_3$O$_3$, 348.13; found 348.2.

Example 2. Isatin Derivative Showed Low IC$_{50}$ in DU145 Prostate Cancer Cell Lines, and A2058 Human Melanoma Cell Lines IC$_{50}$ of values of isatin derivatives Compounds 1~17 and 19~34 were determined in cancer cell lines DU145 and A2058 respectively. DU145 and A2058 cells (5,000 cells/well) were treated with isatin derivatives in a dose-dependent manner (0.05 to 10 µM in 1% DMSO) for 48 hr. Then, MTS assays for cell viability were carried out to determine the $IC_{50}$ values. Four samples were tested for each isatin derivative at each concentration in each cell line, and the averaged data were shown in Table 2a and FIGS. 1~4.

TABLE 2a $IC_{50}$ of Isatin Derivatives Compounds 1~17 and 19~34 in Cancer Cell Lines DU 145 and A2058

| | Test Cell line | |
|---|---|---|
| Compound # | DU145 $IC_{50}$ (µM) | A2058 $IC_{50}$ (µM) |
| 1. | >10 | >10 |
| 2. | 0.79 | 0.78 |
| 3. | 8.5 | 8.4 |
| 4. | 2.4 | 3.8 |
| 5. | >10 | >10 |
| 6. | 4.6 | 6.9 |
| 7. | 4.3 | 4.2 |
| 8. | 5.0 | >5 |
| 9. | 0.47 | 0.66 |
| 10. | >5 | >5 |
| 11. | >5 | >5 |
| 12. | 0.91 | 2.0 |
| 13. | 2.5 | 2.3 |
| 14. | >5 | >5 |
| 15. | >5 | >5 |
| 16. | 0.9 | 1.8 |
| 17. | FIG. 3 | FIG. 4 |
| 19. | >5 | >5 |
| 20. | >5 | 2.5 |
| 21. | >5 | 3.2 |
| 22. | 0.30 | 0.21 |
| 23. | 4.2 | 5.9 |
| 24. | 2.5 | 2.9 |
| 25. | 1.5 | 2 |
| 26. | 0.53 | 0.70 |
| 27. | 0.36 | 0.40 |
| 28. | 1.3 | 1.6 |
| 29. | 0.33 | 0.30 |
| 30. | 0.87 | 1.4 |
| 31. | 0.26 | 0.35 |
| 32. | 4.1 | 1.9 |
| 33. | >5 | >5 |
| 34. | >5 | >5 |

$IC_{50}$ of values of isatin derivatives Compounds 101~123 were determined in cancer cell lines DU145 and A2058 respectively. DU145 and A2058 cells (5,000 cells/well) were treated with isatin derivatives in a dose-dependent manner (0.05 to 10 µM in 1% DMSO or water for 48 hr. Then, MTS assays for cell viability were carried out to determine the $IC_{50}$ values. Four samples were tested for each isatin derivatives at each concentration in each cell line, and the averaged data were shown in Table 2b.

TABLE 2b $IC_{50}$ of Isatin Derivatives Compounds 101~123 in Cancer Cell Lines DU 145 and A2058

| | $IC_{50}$ value (µM) | | | |
|---|---|---|---|---|
| | DMSO | | Water | |
| Compound # | A2058 | DU145 | A2058 | DU145 |
| 101 | 2.2 | 2.1 | N/D | N/D |
| 102 | 3.7 | 4.1 | N/D | N/D |
| 103 | 4.4 | 4.3 | N/D | N/D |

TABLE 2b-continued $IC_{50}$ of Isatin Derivatives Compounds 101~123 in Cancer Cell Lines DU 145 and A2058

| | $IC_{50}$ value (µM) | | | |
|---|---|---|---|---|
| | DMSO | | Water | |
| Compound # | A2058 | DU145 | A2058 | DU145 |
| 104 | 2.1 | 0.91 | N/D | N/D |
| 105 | 4.8 | 2.5 | 4.7 | 4.6 |
| 106 | 1.4 | 0.74 | N/D | N/D |
| 107 | 2.0 | 0.96 | 1.6 | 0.74 |
| 108 | 0.5 | 0.45 | N/D | N/D |
| 109 | 0.58 | 0.48 | 1.0 | 0.63 |
| 110 | 0.58 | 0.47 | N/D | N/D |
| 111 | 0.58 | 0.48 | 0.84 | 0.5 |
| 112 | >5 | >5 | N/D | N/D |
| 113 | >5 | >5 | >5 | >5 |
| 114 | 0.65 | 1.0 | N/D | N/D |
| 115 | 0.68 | 1.4 | 1.9 | 1.9 |
| 116 | 0.39 | 0.66 | N/D | N/D |
| 117 | 1.9 | 3.4 | N/D | N/D |
| 118 | 3.3 | >5 | N/D | N/D |
| 119 | 1.4 | 2.3 | N/D | N/D |
| 120 | 1.2 | 2.3 | 1.9 | 4.1 |
| 121 | 0.35 | 0.5 | N/D | N/D |
| 122 | 0.38 | 0.58 | N/D | N/D |
| 123 | 0.38 | 0.6 | 0.8 | 2.3 |

Note: N/D means not determined.

Example 3. Compound 2 and Compound 22 Reduced Cell Viability in Pancreatic Cancer (PANC-1 and/or PaCa2) Cells Each type of cells (5,000 or 10,000 cells/well) were treated with different concentration (0.1 µM to 10 µM in 1% DMSO of Compound 2 or Compound 22 respectively for 48 hr). Then, MTS assays for cell viability were carried out to determine the $IC_{50}$ values. Four samples were tested for each test compound at each concentration for each type of cells, and the averaged data were shown in Table 3 and FIG. 5.

TABLE 3

$IC_{50}$ of Compound 2 and Compound 22 in Pancreatic Cancer Dells

| | Test cells | |
|---|---|---|
| | PANC-1 | PaCa2 |
| Compound 2 $IC_{50}$ (µM) | 0.97 | N/D |
| Compound 22 $IC_{50}$ (µM) | 0.1 | 0.096 |

Example 4. Compounds 2, 9, 12, 16 and 22 Reduced Cell Viability in Ovarian Cancer (SKOV3, OVCAR5, and/or A2780 Cisplatin-Resistant Ovarian Cancer Cells) Cells Each type of cells (5,000 or 10,000 cells/well) were treated with different concentration (0.1 µM to 20 µM in 1% DMSO of cisplatin or Compound 2, 9, 12, 16 or 22 respectively for 48 hr). Then, MTS assays for cell viability were carried out to determine the $IC_{50}$ values. Four samples were tested for each test compound at each concentration for each type of cells, and the averaged data were shown in Table 4 and FIGS. 6-8.

TABLE 4

IC$_{50}$ of Compounds 2, 9, 12, 16 and 22 in Ovarian Cancer Cells

| Test cells | SKOV3 | OVCAR5 | A2780 cisplatin-resistant |
|---|---|---|---|
| Compound 2 IC$_{50}$ (μM) | >5 | 0.8 | N/D |
| Compound 9 IC$_{50}$ (μM) | N/D | 0.84 | 0.75/0.39 |
| Compound 12 IC$_{50}$ (μM) | N/D | 2.2 | 0.9 |
| Compound 16 IC$_{50}$ (μM) | N/D | 1.7 | 0.5 |
| Compound 22 IC$_{50}$ (μM) | N/D | 0.34 | 0.44 |

FIG. 9 showed that Compound 9 significantly reduced the viability of A2780 cisplatin-resistant ovarian cancer cells in comparison of cisplatin.

Example 5. Compound 9, Compound 22 and Compound 109 Reduced Cell Viability in Lymphoma Cells Such as OCI-Ly3 Non-Hodgkins B Cells Lymphoma Cells, Daudi B Cell Burkitt Lymphoma Cells, and/or Anaplastic Large T Cells Lymphoma Cells Each type of cells (5,000 or 10,000 cells/well) were treated with different concentration (0.01 μM to 5 μM in 1% DMSO of the test compound respectively for 48 hr). Then, MTS assays for cell viability were carried out to determine the IC$_{50}$ values. Four samples were tested for each test compound at each concentration for each type of cells, and the averaged data were shown in Table 5 and FIGS. 10~12.

TABLE 5

IC$_{50}$ (μM) of Compounds 9, 22 and 109 in Lymphoma Cells

| Test cells | OCI-Ly3 non-Hodgkins B cell lymphoma cells | Daudi B Cell Burkitt lymphoma cells | Anaplastic Large T cell lymphoma cells |
|---|---|---|---|
| Compound 9 IC$_{50}$ (μM) | 0.26 | N/D | N/D |
| Compound 22 IC$_{50}$ (μM) | 0.039 | 0.038 | 0.13 |
| Compound 109 IC$_{50}$ (μM) | 0.063 | N/D | N/D |

Example 6. Compound 2 Showed Inhibition of Phosphorylation of EGFR and Erk1/2 in DU145 Prostate Cancer Cells. (FIG. 13)

DU145 prostate cancer cells were incubated in complete growth medium in 100 mm petri dishes (1×10$^6$ cells per dish) for 24 hr. Compound 2 was added at a concentration of 0.5 μM, 1.0 μM, 2.5 μM, and 5 μM respectively. Cell samples that were not added any Compound 2 were negative controls. After 4 hr, EGF (10 ng/ml final concentration) was added to culture media and cells were lysed using Laemmli buffer. Differences in the phosphorylation of Erk1/2 and EGFR were determined by immunoblot analysis (FIG. 13).

The results showed less phosphorylations of EGFR and Erk1/2 were observed in the cell samples treated with Compound 2 compared to the negative control in a concentration-associate manner. Higher concentration of Compound 2 showed enhanced inhibition to phosphorylations of EGFR and Erk1/2.

Example 7. Compound 2 Showed Inhibition of Phosphorylation of Her2/Neu, Jak2, Src, Stat3, AKT, and Erk1/2 in A2058 Melanoma Cells. (FIGS. 14a and 14b)

A2058 melanoma cells were incubated in complete growth medium in 100 mm petri dishes (1×10$^6$ cells per dish) for 24 hr. Compound 2 was added at a concentration of 0.5 μM, 1.0 μM, 2.5 μM, and 5 μM respectively. Cell samples that were not added any Compound 2 were negative controls. After 4 hr, cells were lysed using Laemmli buffer. Differences in the phosphorylation of Her2/Neu, Jak2, Src, Stat3, AKT, and Erk1/2 were determined by immunoblot analysis (FIG. 14a).

The results showed less phosphorylations of Her2/Neu, Jak2, Src, Stat3, AKT, and Erk1/2 were observed in the cell samples treated with Compound 2 compared to the negative control in a concentration-associated manner. Higher concentration of Compound 2 showed enhanced inhibition to phosphorylations of Her2/Neu, Jak2, Src, Stat3, Akt, and Erk1/2.

A2058 melanoma cells were incubated in complete growth medium in 100 mm petri dishes (1×10$^6$ cells per dish) for 24 hr. Compound 2 was added at a concentration of 5 μM. Cell samples that were not added any Compound 2 were negative controls. Cells were lysed using Laemmli buffer 0.5 hr, 1 hr, 2 hr, 4 hr, 6 hr and 24 hr after treatment. Differences in the phosphorylation of Jak2, Src, Stat3, AKT, and Erk1/2 were determined by immunoblot analysis (FIG. 14b).

Example 8. Effect of Compound 22 on Cell Cycle (Cyclin B1, p-Cdc25C, and Actin) of DU145 Prostate Cancer Cells and A2058 Melanoma Cells (FIG. 15)

DU145 prostate cancer cells or A2058 melanoma cells were incubated with Compound 22 at a concentration of 0.1, 1, or 2.5 μM or DMSO for 24 hr. Cells were lysed using Laemmli buffer. The differences in the content of Cyclin B1 and phosphorylation of Cdc25C were determined by immunoblot analysis. The results showed that cells treated with a higher dosage of Compound 22 had increased amount of Cyclin B1 and less phosphorylation of Cdc25C (FIG. 15).

Example 9. Compound 22 Showed Inhibition of Microtubule Formation in In Vitro Tubulin Polymerization Assay To determine whether Compound 22 inhibits tubulin formation in vitro, HTS-Tubulin polymerization assay kits (cytoskeleton) were used. The assay procedure was performed using the manufacturer's protocol. Briefly, each 4 mg tubulin was resuspended with 1 mL of the cold G-PEM (80 mM PIPES pH6.9, 2 mM MgCl$_2$, 0.5 mM EGTA) buffer to make the final concentration of 4 mg/mL. The reaction volume was 100 μL. Tubulin polymerization was monitored with the kinetic mode at 340 nM for 1 hr at 37° C. Compound 22 substantially inhibited tubulin polymerization in vitro at 1 μM concentration, suggesting that Compound 22 reduced microtubule polymerization in cells. Together, compound 22 is a promising lead compound to develop new anticancer drugs as new class of microtubule inhibitors.

Example 10. Compound 109 (JX9) Showed Efficacy in Treating Ly-3 Lymphoma SQ Xenografts Ly-3 lymphoma cells (1×10$^7$) were subcutaneously injected to Il-2 rg(ko)/NOD-SCID female mice. 7 mice were treated with vehicle as the control group once a day. 7 mice were treated with Compound 109 as the treatment group by oral administration at 100 mg/kg dose, once a day. Mice were euthanized at the 7th treatment day by IACUC of the Beckman Research Institute of City of Hope. Tumor volumes were measured and shown in FIG. 17. In the figure, * means P=0.03 wherein P values less than 0.05 were considered statistically significant. Thus, Compound 109 statistically significantly showed efficacy in the in vivo study.

The following references and references cited supra are incorporated herein by reference as if fully set forth herein 1. Fedchenko V, Globa A, Kaloshin A, Kapitsa I, Nerobkova L, Val'dman E, Buneeva O, Glover V, Medvedev A. The effect of short-term administra-tion of (−)-deprenyl and isatin on the expressions of some genes in the mouse brain cortex. Med. Sci. Monit. 2008, 14: 69~73.
2. Pandeya S N, Sriram D. Synthesis and screening for an-tibacterial activity of Schiff's and Mannich bases of Isatin and its derivatives. Acta. Pharm. Turc. 1998, 40:33~38.
3. Sarangapani M, Reddy V M. Synthesis and antimicrobial activity of 1-[(N,N-disubstituted amino) methyl]-3-[(2-phenyl-3,4-dihydro-4-oxoquinazoline-3-yl] in-dole-2-one. Indian J. Heterocycl. Chem. 1994, 3:257~260.
4. Varma R S, Nobles W L. Antiviral, antibacterial, and anti-fungal activities of isatin N-Mannich bases. J. Pharm. Sci. 1975, 64: 881~882.
5. Loncle C, Brunel J M, Vidal N, Dherbomez M, Letourneux Y. Synthesis and antifungal activity of choles-terol-hydrazone derivatives. Eur. J. Med. Chem. 2004, 39:1067~1071.
6. Papakonstantinou-Garoufalias S, Pouli N, Marakos P, Chytyroglou-Ladas A. Synthesis antimicrobial and an-tifungal activity of some new 3-substituted deriva-tives of 4-(2,4-dichlorophenyl)-5-adamantyl-1H-1,2,4-triazole. II Farmaco 2002, 57: 973~977.
7. Vicini P, Zani F, Cozzini P, Doytchinova I. Hydrazones of 1,2-benzisothiazole hydrazides: synthesis, antimi-crobial activity and QSAR investigations. Eur. J. Med. Chem. 2002, 37: 553~564.
8. Sridhar S K, Pandeya S N, Stables J P, Ramesh A. The Wide Pharmacological Versatility of Semicarbazones, Thiosemicarbazones and Their Metal Complexes. Eur. J. Med. Chem. 2002, 16: 129~132.
9. Varma M, Pandeya S N, Singh K N, Stables J P. Anticonvulsant activity of Schiff bases of isatin derivatives. Acta Pharm. 2004, 54: 49~56.
10. Popp F D. Potential anticonvulsant. XII. Anticonvulsant activity of some aldehyde derivatives. Eur. J. Med. Chem. 1989, 24:313~315.
11. Küçükgüzel S G, Rollas S, Küçükgüzel I, Kiraz M. Synthe-sis and antimycobacterial activity of some coupling products from 4-aminobenzoic acid hydrazones. Eur. J. Med. Chem. 1999, 34:1093~1100.
12. Papakonstantinou-Garoufalias S, Pouli N, Marakos P, Chytyroglou-Ladas A. Synthesis antimicrobial and an-tifungal activity of some new 3-substituted deriva-tives of 4-(2,4-dichlorophenyl)-5-adamantyl-1H-1,2,4-triazole. II Farmaco 2002, 57: 973~977.
13. Pandeya S N, Sriram D, Nath G, De Clercq E. Synthesis, antibacterial, antifungal and anti-HIV activities of Schiff and Mannich bases derived from isatin deriva-tives and N-[4-(4'-chlorophenyl)thiazol-2-yl] thiose-micarbazide. Eur. J. Pharm. Sci. 1999, 9: 25~31.
14. Pandeya S N, Sriram D, Nath G, De Clercq E. Synthesis, antibacterial, antifungal and anti-HIV activity of Schiff and Mannich bases of isatin with N-[6-chlorobenzthiaz-ole-2-yl] thiosemicarbazide. Indian J. Pharm. Sci. 1999, 61: 358~361.
15. Pandeya S N, Sriram D, Nath G, De Clercq E. Synthesis, antibacterial, antifungal and anti-HIV evaluation of Schiff and Mannich bases of isatin derivatives with 3-amino-2-methylmercapto quinazolin-4(3H)-one. Pharm. Acta Helv. 1999, 74: 11~17.
16. Varma R S, Nobles W L. Synthesis and antiviral and anti-bacterial activity of certain N-dialkylaminomethyli-satin beta-thiosemicarbazones. J. Med. Chem. 1967, 10: 972~974.
17. Singh S P, Shukla S K, Awasthi L P. Synthesis of some 3-(4'-nitrobenzoylhydrazono)-2-indolinones as a po-ten-tial antiviral agents. Curr. Sci. 1983, 52: 766~769.
18. Logan J C, Fox M P, Morgan J H, Makohon A M, Pfau C J. Arenavirus inactivation on contact with N-substituted isatin β-thiosemicarbazones and certain cations. J. Gen. Virol. 1975, 28: 271~283.
19. Zhou L, Liu Y, Zhang W, Wei P, Huang C, Pei J, Yuan Y, Lai L. Isatin Compounds as Noncovalent SARS Coronavirus 3C-like Proteasa Inhibitors. J. Med. Chem. 2006, 49: 3440~3443.
20. Pandeya S N, Sriram D, Nath G, De Clercq E. Synthesis, antibacterial, antifungal and anti-HIV evaluation of Schiff and Mannich bases of isatin derivatives with 3-amino-2-methylmercapto quinazolin-4(3H)-one. Pharm. Acta Helv. 1999, 74: 11~17.
21. Pandeya S N, Sriram D, Nath G, De Clercq E. Synthesis, antibacterial, antifungal and anti-HIV activities of Norfloxacin Mannich bases. Eur. J. Med. Chem. 2000, 35: 249~255.
22. Pandeya S N, Sriram D, Nath G, De Clercq E. Synthesis, antibacterial, antifungal and anti-HIV evaluation of Schiff and Mannich bases of isatin and its derivatives with triazole. Arzneim. Forsch./Drug Res. 2000, 50: 55~59.
23. Imam S A, Varma R S. Isatin-3-anils as excystment and cysticidal agents against Schizopyrenus russelli. Ex-peri-entia 1975, 31:1287~1288.
24. Varma R S, Khan I A. Potential biologically active agents. X. Synthesis of 3-arylimino-2-indolinones, and their 1-methyl- and 1-morpholino/piperidinomethyl deriv-atives as excystment and cysticidal agents against Schizopyrenus russelli. From Polish journal of phar-macology and pharmacy 1977, 29: 549~594.
25. Sarciron M E, Audin P, Delebre I, Gabrion C, Petavy A F, Paris J. Synthesis of propargylic alcohols and biological effects on Echinococcus multilocularis metaces-todes. J. Pharm. Sci. 1993, 82: 605~609.
26. El-Sawi E A, Mostaza T B, Mostaza B B. Studies on the molluscicidal action of some isatin derivatives against Biomphalaria alexandrina in Egypt. J. Egypt. Soc. Parasitol. 1998, 28: 481~486.
27. Karah N, Terzioglu N, Gursoy A. Synthesis and structure-activity relationships of 3-hydrazono-1H-2-indolinones with antituberculosis activity. Arzneimit-tel-Forsc-hung 1998, 48: 758~763.
28. Sriram D, Yogeeswari P, Gopal G. Synthesis, anti-HIV and antitubercular activities of lamivudine prodrugs. Eur. J. Med. Chem. 2005, 40:1373~1376.
29. Küçükgüzel S G, Rollas S, Küçükgüzel I, Kiraz M. Synthe-sis and antimycobacterial activity of some coupling products from 4-aminobenzoic acid hydrazones. Eur. J. Med. Chem. 1999, 34:1093~1100.
30. Kaymakçioğlu B K, Rollas S. Synthesis, characterization and evaluation of antituberculosis activity of some hydrazones. II Farmaco 2002, 57: 595~599.
31. Patole J, Sandbhor U, Padhye S, Deobagkar D N, Anson C E, Powell A. Structural chemistry and In vitro anti-tubercular activity of acetylpyridine benzoyl hydra-zone and its copper complex against Mycobacterium smegma-tis. Bioorg. Med. Chem. Lett. 2003, 13:51~55.

32. Maccari R, Ottanà R, Vigorita M G. In vitro advanced antimycobacterial screening of isoniazid-related hy-drazones, hydrazides and cyanoboranes: Part 14. Bioorg. Med. Chem. Lett. 2005, 15: 2509~2513.
33. Cocco M T, Congiu C, Onnis V, Pusceddu M C, Schivo M L, Logu A. Synthesis and antimycobacterial activity of some isonicotinoylhydrazones. Eur. J. Med. Chem. 1999, 34: 1071~1076.
34. Karali N, Kocabalkanli A, Gürsoy A, Ateş Ö. Synthesis and antitubercular activity of 4-(3-coumarinyl)-3-cyclohexyl-4-thiazolin-2-one benzylidenehydrazones. II Farmaco 2002, 57: 589~593.
35. Rando D G, Sato D N, Siqueira L, Malvezzi A, Leite C Q F, Amaral A T, Ferreira E I, Tavares L C. Potential tubercu-lostatic agents. Topliss application on benzoic acid [(5-Nitro-thiophen-2-yl)-methylene]-hydrazide se-ries. Bioorg. Med. Chem. 2002, 10: 557~560.
36. Holla B S, Rao B S, Shridhara K, Akberali P M. Studies on arylfuran derivatives. Part XI. Synthesis, characterization and biological studies on some Mannich base carrying 2,4-dichlorophenylfurfural moiety. Farmaco 2000, 55:338~344.
37. Pandeya S N, Smitha S, Jyoti M, Sridhar S K. Biological activities of isatin and its derivatives. Acta Pharm. 2005, 55: 27~46.
38. Pal R, Jain K, Gupta G D, Handa R N, Puzari H K. Synthetic methods using isatin and derivatives. Indian J. Chem. 19991, 30B: 1098.
39. Chiyanzu I, Clarkson C, Smith P J, Lehman J, Gut J, Ro-senthalc P J, Chibalea K. Design, synthesis and anti-plasmodial evaluation in vitro of new 4-aminoquinoline isatin derivatives. Bioorg. Med. Chem. 2005, 13, 3249~3261.
40. Melnyk P, Leroux V, Sergheraert C, Grellier P. Design, synthesis and in vitro antimalarial activity of an acyl-hydrazone library. Bioorg. Med. Chem. Lett. 2006, 16: 31~35.
41. Todeschini A R, Miranda A L P, Silva K C M, Parrini S C, Barreiro E J. Synthesis and evaluation of analgesic, antiinflammatory and antiplatelet properties of new 2-pyridylarylhydrazone derivatives. Eur. J. Med. Chem. 1998, 33: 189~199.
42. Gaston M A, Dias L R S, Freitas A C C, Miranda A L P, Barrei-ro EJ. Synthesis and analgesic properties of new 4-arylhydrazone 1-H pyrazole [3,4-b]pyridine derivatives. Pharmac. Acta Helvet. 1996, 71: 213~219.
43. Aboul-Fadl T, Mohammed F A, Hassan E A. Synthesis, Antitubercular Activity and Pharmacokinetic Studies of Some Schiff Bases Derived from 1-Alkylisatin and Isonicotinic Acid Hydrazide (INH). Arch. Pharm. Res. 2003, 26: 778~784.
44. Burger's Medicinal Chemistry And Drug Discovery, 5th Edition, Vol 1: Principles and Practice.
45. Yoshida M, Asano M, Omichi H, Hayashi Y, Yamaguchi I, MatsudaInt K. Study of biodegradable copoly(l-lactic acid/glycolic acid) formulations with controlled release of Z-100 for application in radiation therapy. Int. J. Pharm. 1995, 115:61~67 (1995).
46. Gregoriadis, Liposome Technology, Vols. I to III, 2nd ed. (CRC Press, Boca Raton Fla. (1993).
47. Physician's Desk Reference, 41st Ed., Publisher Edward R. Barnhart, N.J. (1987).
48. PCT/US93/00829.
49. U.S. Pat. No. 3,773,919.
50. EP 58,481.
51. Sidman K R, Steber W D, Schwope A D and Schnaper G R. Controlled release of macromolecules and pharmaceuticals from synthetic polypeptides based on glutamic acid Biopolymers, 1983, 22:547~556.
52. Langer R, Brem H, and Tapper D. Biocompatibility of polymeric delivery systems for macromolecules. J. Biomed. Mater. Res., 1981, 15:167~277.
53. Langer et al., Chem. Tech., 1982, 12:98~105.
54. EP 133,988.
55. Epstein D A, Marsh Y V, Van der Pas M, Feigner P L, and Schreiber A B. Biological activity of liposome-encapsulated murine interferon gamma is mediated by a cell membrane receptor. Proc. Natl. Acad. Sci. (USA), 82:3688-3692 (1985).
56. EP 36,676.
57. EP 88,046.
58. EP 143,949.
59. Overman L E, and Peterson E A. Enantioselective synthesis of (−)-idiospermuline. Tetrahedron 2003, 59, 6905~6919.
60. Marti C and Carreira E M. Carreira, E. M. Total Synthesis of (−)-Spirotryprostatin B: Synthesis and Related Studies. J. Am. Chem. Soc. 2005, 127, 11505~11515.
61. Trost B M and Frederiksen M U. Palladium-Catalyzed Asymmetric Allylation of Prochiral Nucleophiles: Synthesis of 3-Allyl-3-Aryl Oxindoles. Angew. Chem. Int. Ed. 2005, 44, 308~310.
62. Molander G A, and Ellis N. Acc. Organotrifluoroborates: Protected Boronic Acids That Expand the Versatility of the Suzuki Coupling Reaction. Chem. Res. 2007, 40, 275~286.
63. Wang J-J, and Hu W-P J. Novel 3-Aza-Grob Fragmentation in Hydride Reduction of Ether-Protected Aromatic Lactams. Org. Chem. 1999, 64, 5725~5727.
64. Hamada T, Okuno Y, Ohmori M, Nishi T, and Yonemitsu O. Photochemical Synthesis of 1, 2, 3, 4-Tetrahydroisoquinolin-3-ones and Oxindoles from N-Chloroacetyl Derivatives of Benzylamines and Anilines. Role of Intramolecular Exciplex Formation and cis Conformation of Amide Bonds. Chem. Pharm. Bull. 1981, 29, 128~136.

The invention claimed is:

1. An isatin derivative comprising a structure of Structure I:

Structure I and the pharmaceutically acceptable solvates, salts and stereoisomers thereof, including mixtures thereof in all ratios wherein:

Y is C;

$R_1$ is selected from the group consisting of H, and halogen;

$R_2$ is heteroaryl substituted with F, Cl, Br, or I;

$R_3$ and $R_4$ are H;

$R_5$ is selected from the group consisting of $R_{50}$, $R_{50}$—$R_{51}$, $R_{50}$—OH, and $R_{50}$—O—$R_{51}$—OH;

$R_{50}$ is selected from the group consisting of C1~C6 alkyl, C2~C6 alkenyl, methyl, ethyl, propyl, butyl, and —C—C=C—;

$R_{51}$ is selected from the group consisting of phenyl, heteroaryl, groups comprising one or more atoms selected from the group consisting of N, O and S, pyridinyl, pyrimidinyl, thiophenyl, and furanyl, optionally substituted with F, Cl, Br, I, and/or pyridinyl; and $R_6$ and $R_7$ taken together is =O.

2. The isatin derivative according to claim 1, selected from the group consisting of Compound 29, and Compound 31.

3. A pharmaceutical composition comprising a therapeutically effective amount of at least one isatin derivative according to claim 1 and a pharmaceutically acceptable carrier.

4. The pharmaceutical composition according to claim 3, wherein the isatin derivative is Compound 29 or Compound 31.

5. A method for treating a subject having a cancer or tumor selected from the group consisting of prostate cancer, melanoma, pancreatic cancer, ovarian cancer, and lymphoma comprising administering to the subject a therapeutically effective amount of an isatin derivative according to claim 1.

6. The method according to claim 5, wherein the cancer is prostate cancer, and the isatin derivative is selected from the group consisting of Compound 29 and Compound 31.

7. The method according to claim 5, wherein the cancer is melanoma, and the isatin derivative is selected from the group consisting of Compound 29 and Compound 31.

8. A method of treating a condition that can be regulated by the activation of one or more proteins in a subject comprising administering to the subject a therapeutically effective amount of at least one isatin derivative according to claim 1, or a pharmaceutical composition thereof, wherein the one or more proteins are selected from the group consisting of EGFR, Erk1/2, Her2/Neu, Jak2, Src, Stat3, Akt, Cyclin B1, and Cdc25C, and the condition is a cancer or tumor selected from the group consisting of prostate cancer, melanoma, pancreatic cancer, ovarian cancer, and lymphoma.

* * * * *